United States Patent
Matsuyama

(10) Patent No.: US 9,458,427 B2
(45) Date of Patent: *Oct. 4, 2016

(54) IFNγR2 COMPOSITIONS AND METHODS OF INHIBITING NEURONAL CELL DEATH

(71) Applicant: Case Western Reserve University, Cleveland, OH (US)

(72) Inventor: Shigemi Matsuyama, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 98 days.

This patent is subject to a terminal disclaimer.

(21) Appl. No.: 14/279,432

(22) Filed: May 16, 2014

(65) Prior Publication Data

US 2014/0256039 A1 Sep. 11, 2014

Related U.S. Application Data

(63) Continuation-in-part of application No. 13/679,439, filed on Nov. 16, 2012, which is a continuation of application No. 12/853,122, filed on Aug. 9, 2010, now Pat. No. 8,324,170.

(60) Provisional application No. 61/232,050, filed on Aug. 7, 2009, provisional application No. 61/824,437, filed on May 17, 2013.

(51) Int. Cl.
*A61K 38/04* (2006.01)
*C07K 14/715* (2006.01)
*C12N 5/0793* (2010.01)
*A61K 38/08* (2006.01)
*A61K 38/07* (2006.01)
*C07K 16/28* (2006.01)

(52) U.S. Cl.
CPC ............. *C12N 5/0619* (2013.01); *A61K 38/07* (2013.01); *A61K 38/08* (2013.01); *C07K 14/7156* (2013.01); *C07K 16/2866* (2013.01); *C07K 2317/34* (2013.01); *C07K 2319/01* (2013.01)

(58) Field of Classification Search
None
See application file for complete search history.

(56) References Cited

U.S. PATENT DOCUMENTS

| | | | | |
|---|---|---|---|---|
| 6,696,303 | B2 * | 2/2004 | Gilchrest | C07K 5/0815 |
| 7,314,866 | B2 * | 1/2008 | Matsuyama | A01N 1/02 |
| 7,608,430 | B2 * | 10/2009 | Karow | C07K 14/715 |
| 2006/0246047 | A1 * | 11/2006 | Imoto | C07K 14/4747 |

FOREIGN PATENT DOCUMENTS

WO    WO 02088163 A1 * 11/2002  ......... C12N 15/1138

OTHER PUBLICATIONS

Gomez et al., The C-terminus of interferon gamma receptor beta chain (IFNgR2) has antiapoptotic activity as a Bax inhibitor, Cancer Biol. & Ther. 8(18):1771-1786, Sep. 15, 2009.*

(Continued)

*Primary Examiner* — Claire Kaufman
(74) *Attorney, Agent, or Firm* — Tarolli, Sundheim, Covell & Tummino LLP

(57) ABSTRACT

A method of inhibiting β-amyloid (Aβ) induced neuronal cell death includes administering to a neuronal cell exposed to a neurotoxic amount of Aβ a therapeutically effective amount of cell penetrating peptide (CPP). The CPP has an amino acid sequence that has at least 80% sequence identity to about 5 to about 41 consecutive amino acids of SEQ ID NO: 1.

15 Claims, 15 Drawing Sheets

(56) References Cited

OTHER PUBLICATIONS

Farrar et al. Identifcation of a functionally important sequence in the C terminus of the interferon-gamma receptor, Proc. Natl. Acad. Sci, USA, 89:11706-11710, Dec. 1992.*

Bernabei et al., Inteferon-gamma receptor 2 expression as the deciding factor in human T, B, and myeloid cell proliferation or death, J. Leuk. Biol. 70:950-960, Dec. 2001.*

Bate et al., Interferon-gamma increases neuronal death in response to amyloid-beta1-42, J. Neuroinflamm. 3:7, Mar. 28, 2006.*

Nilsen et al., Estrogen protects neuronal cells from amyloid beta-induced apoptosis via regulation of mitochondrial proteins and function, BMC Neurosci. 7:74, Nov. 3, 2006.*

* cited by examiner

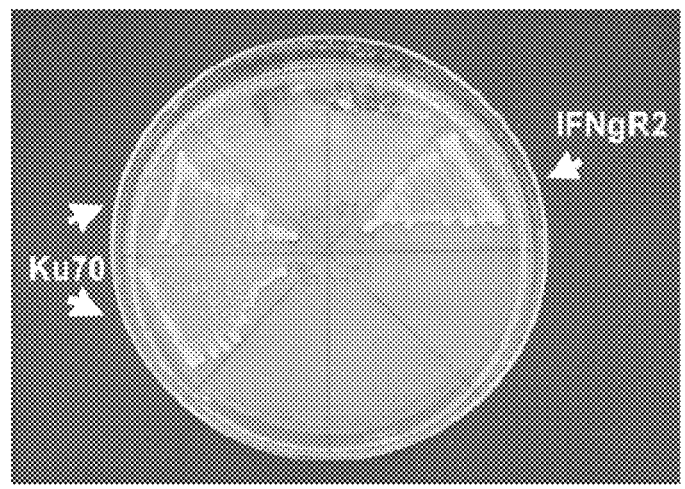
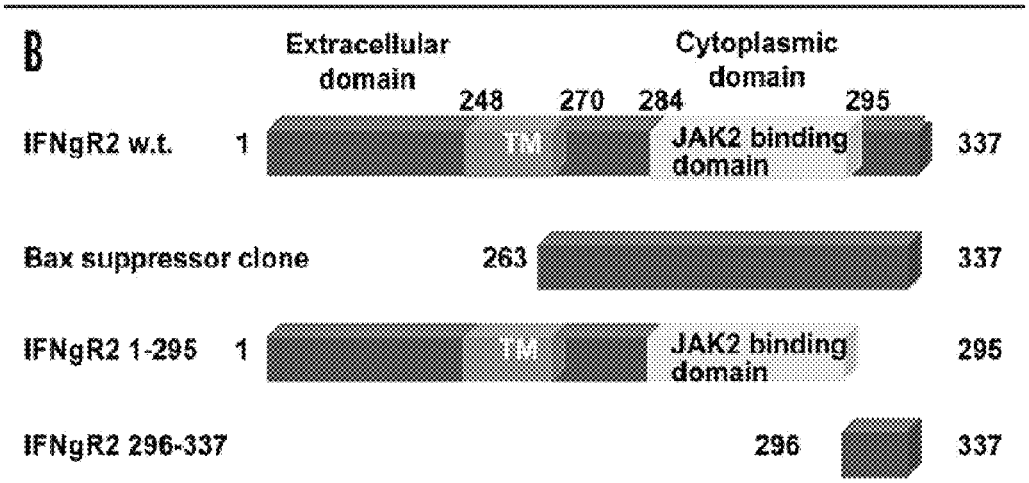
Fig. 1A-B

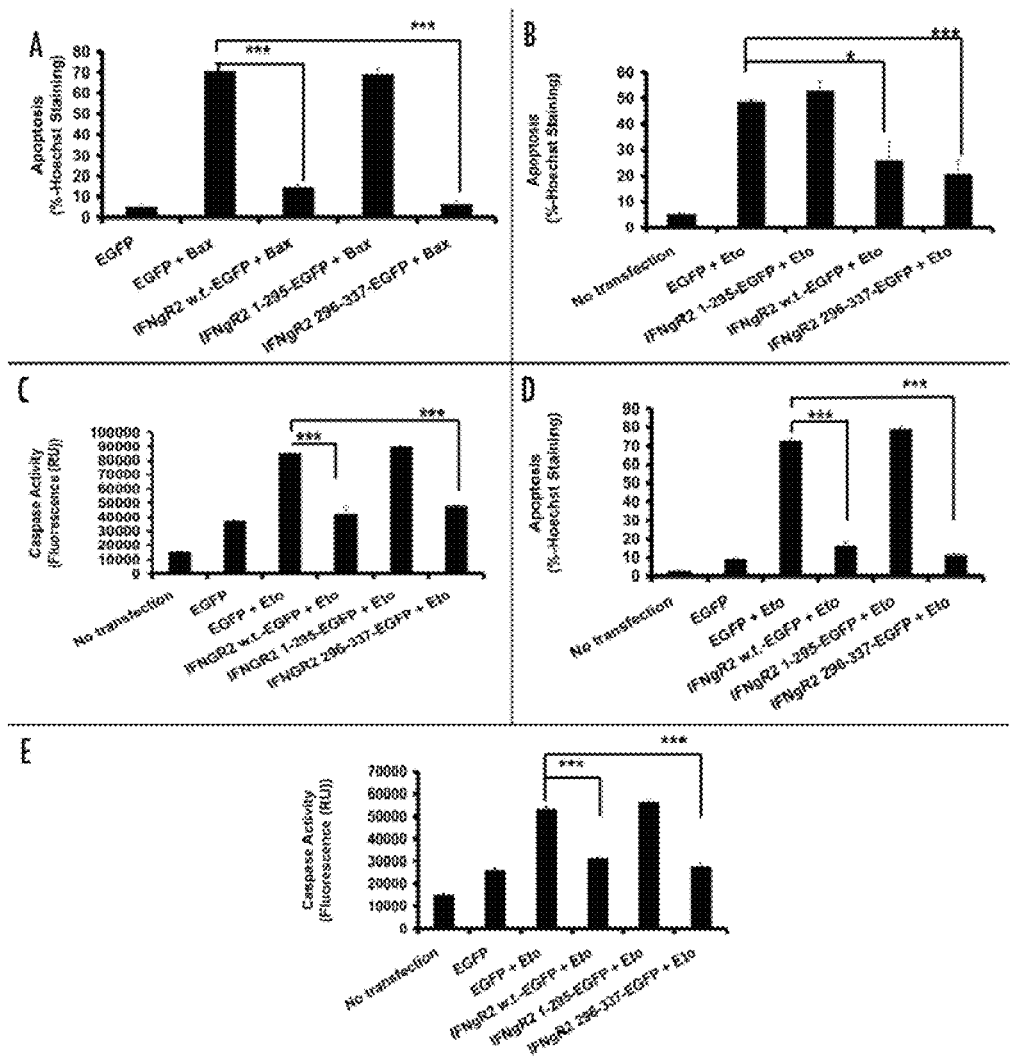
Fig. 2A-E

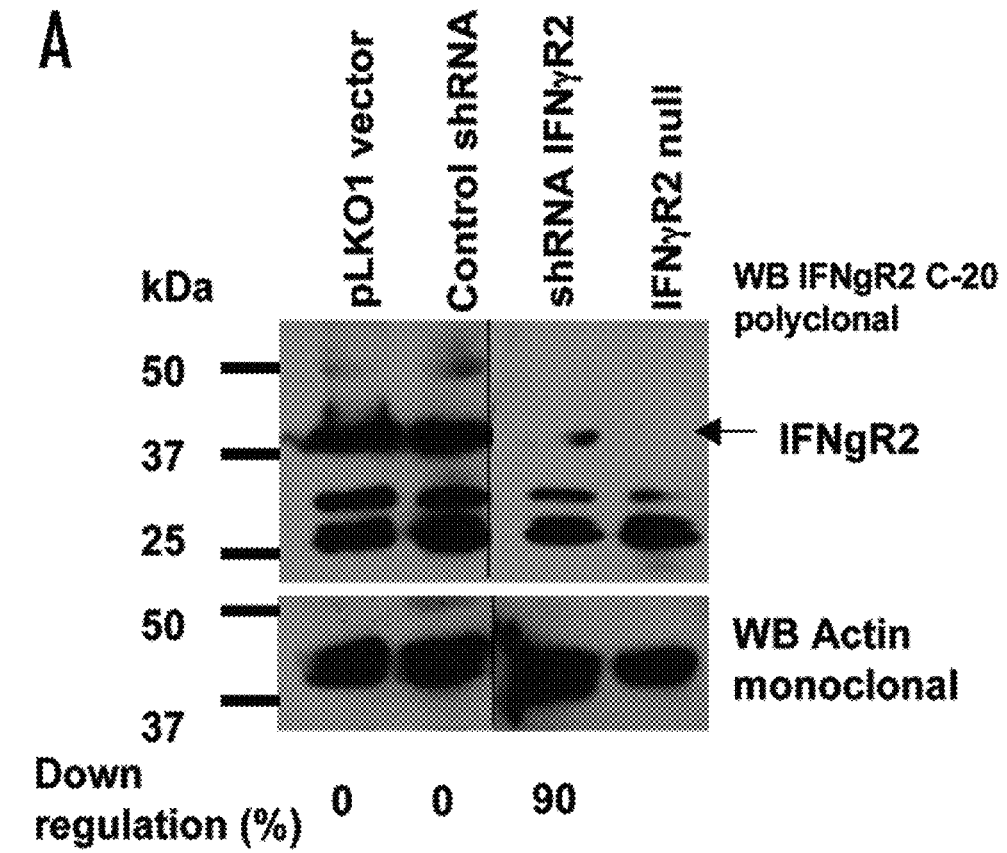
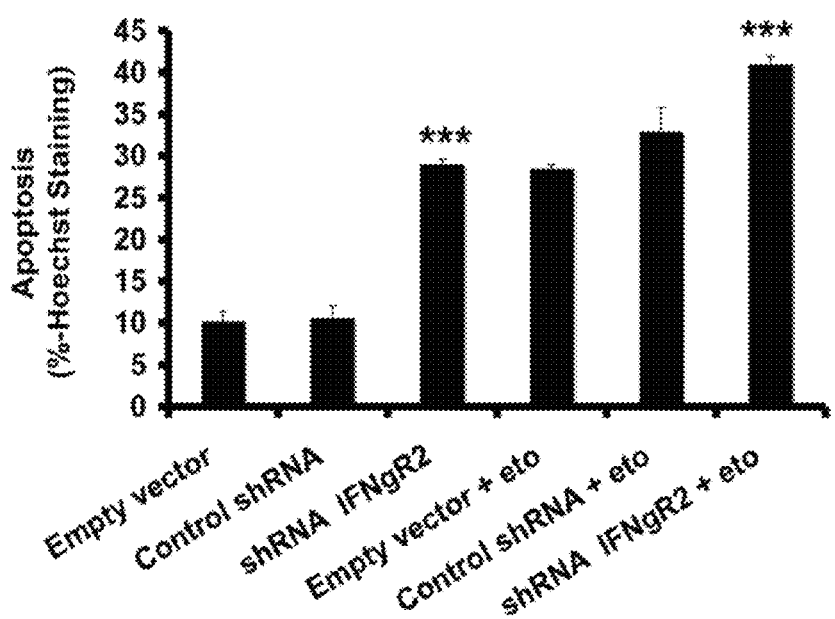
Fig. 3A-B

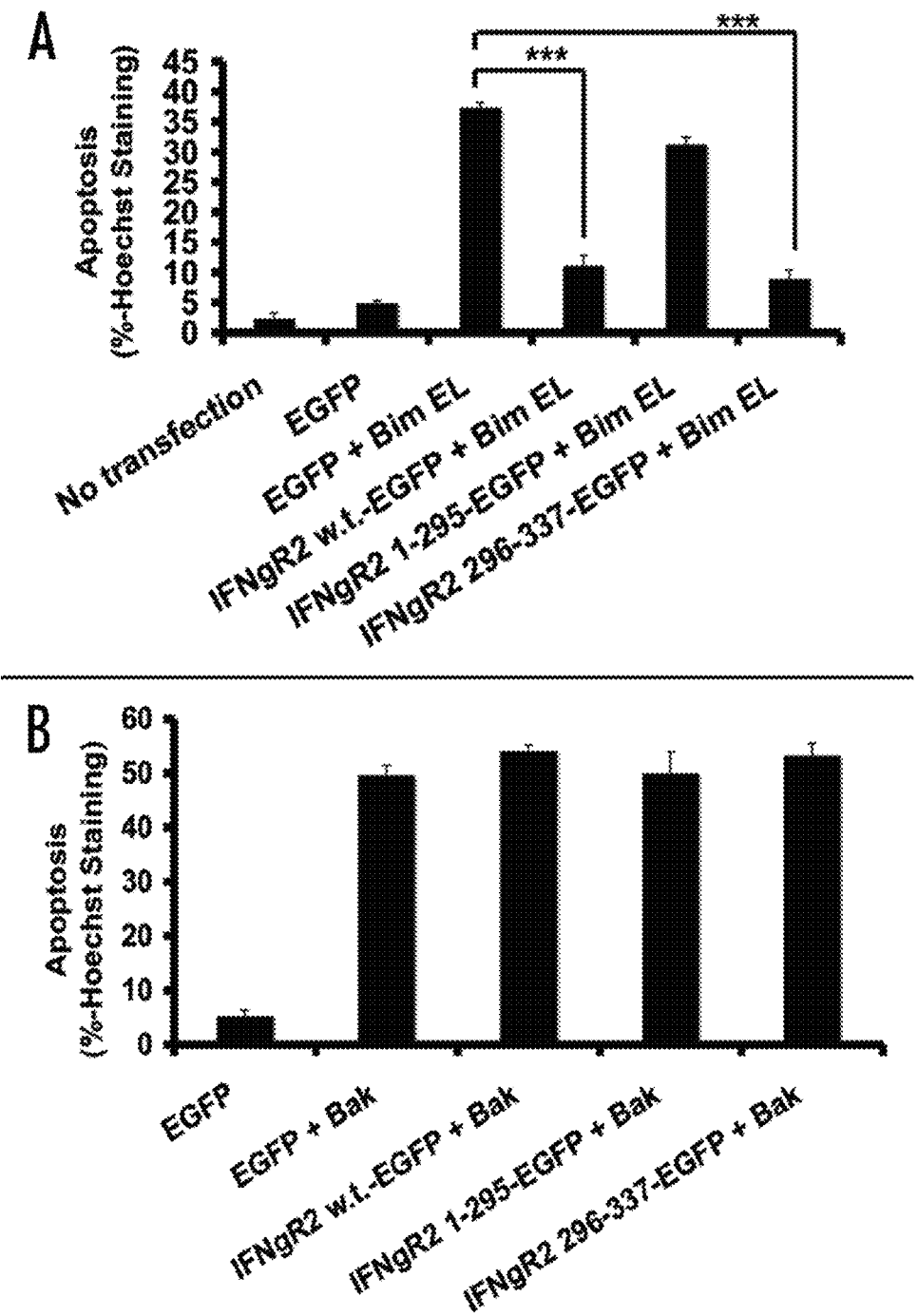
Fig. 4A-B

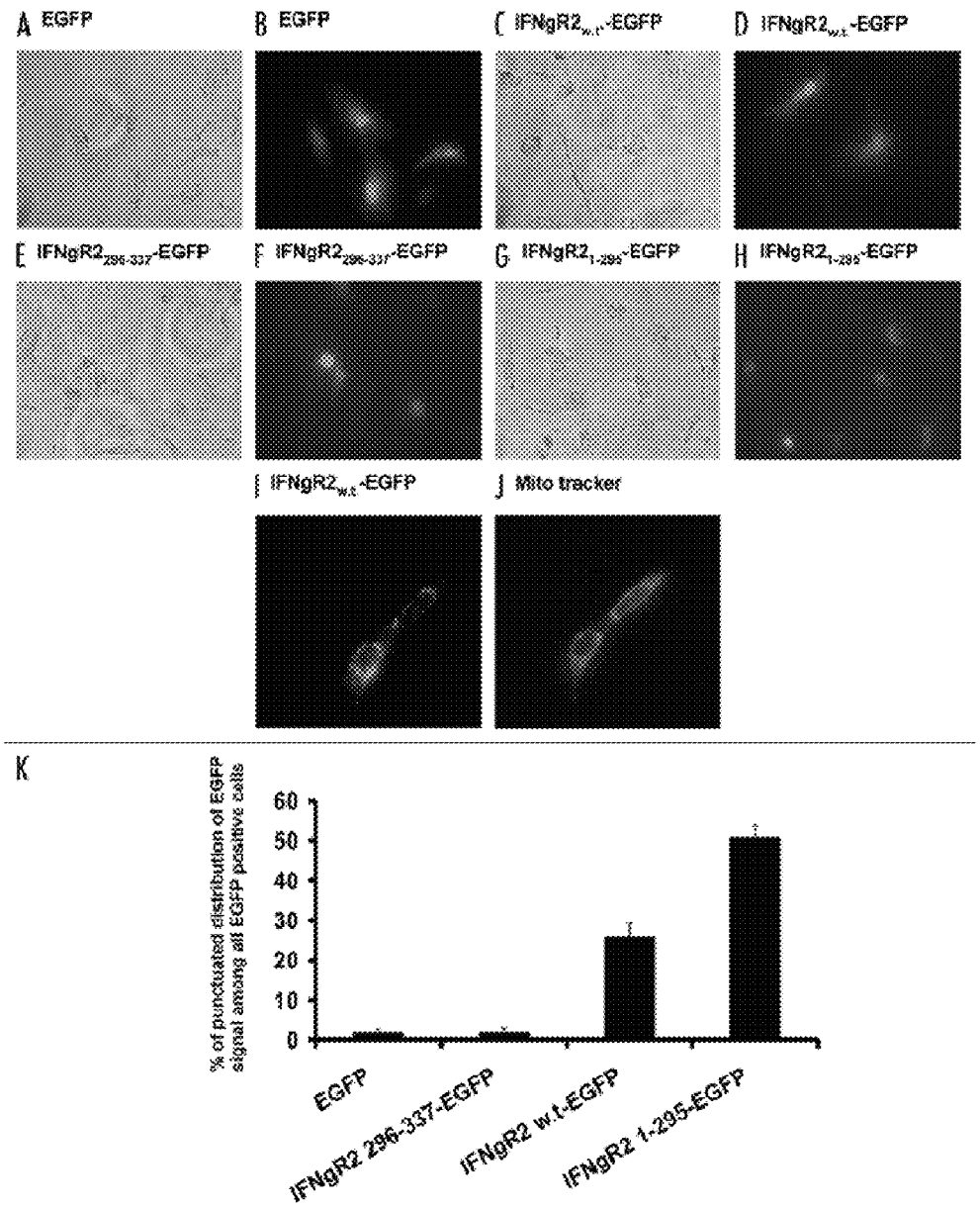
Fig. 5A-K

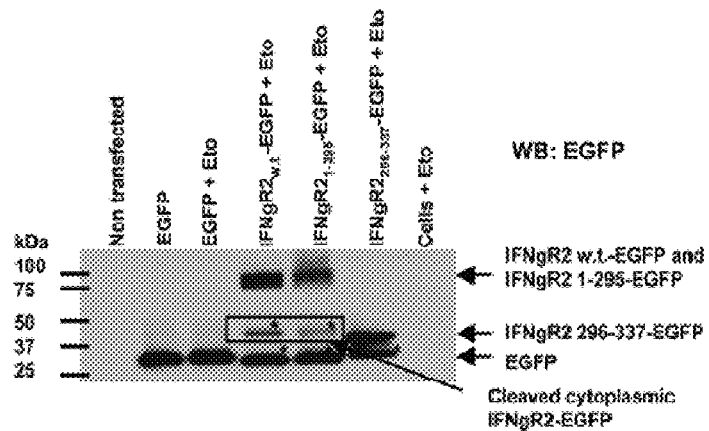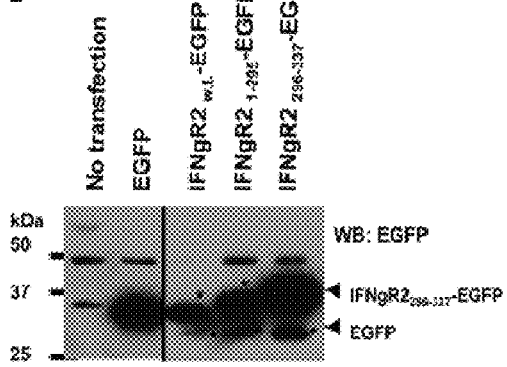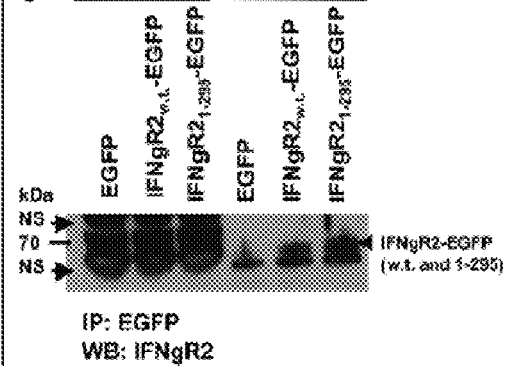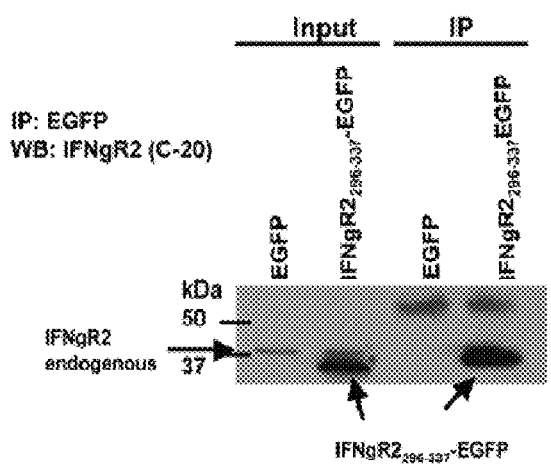
Fig. 6A-D

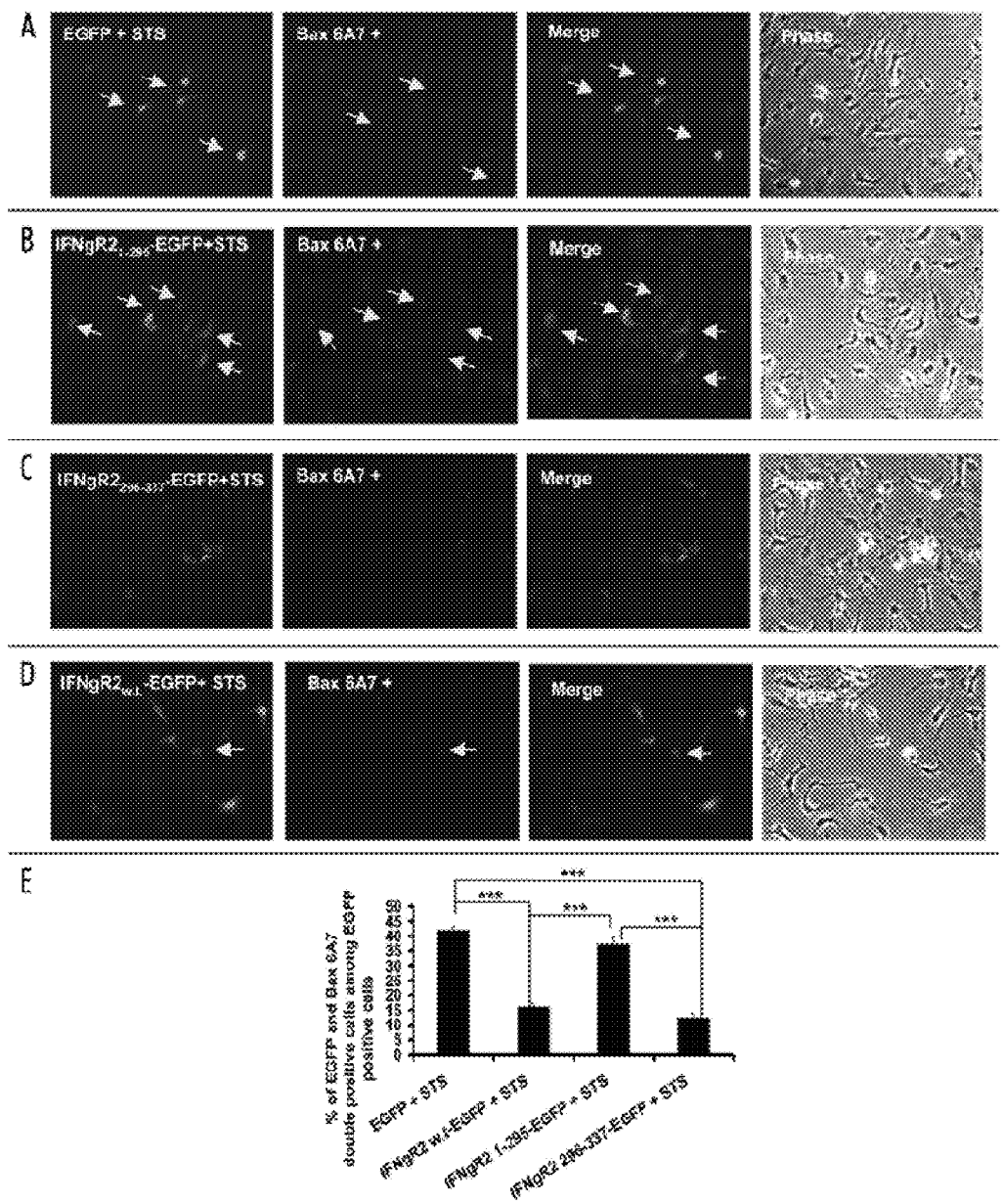
Fig. 7A-E

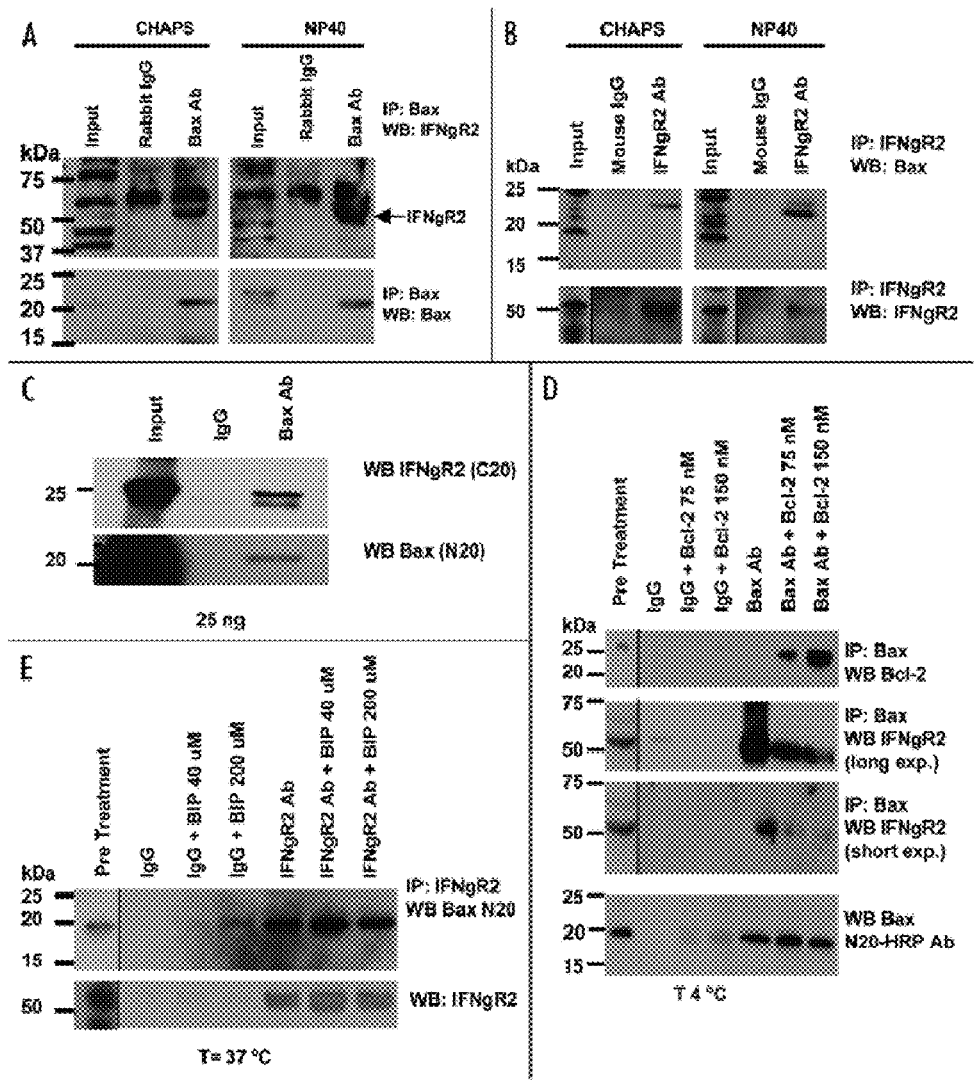
Figs. 8A-E

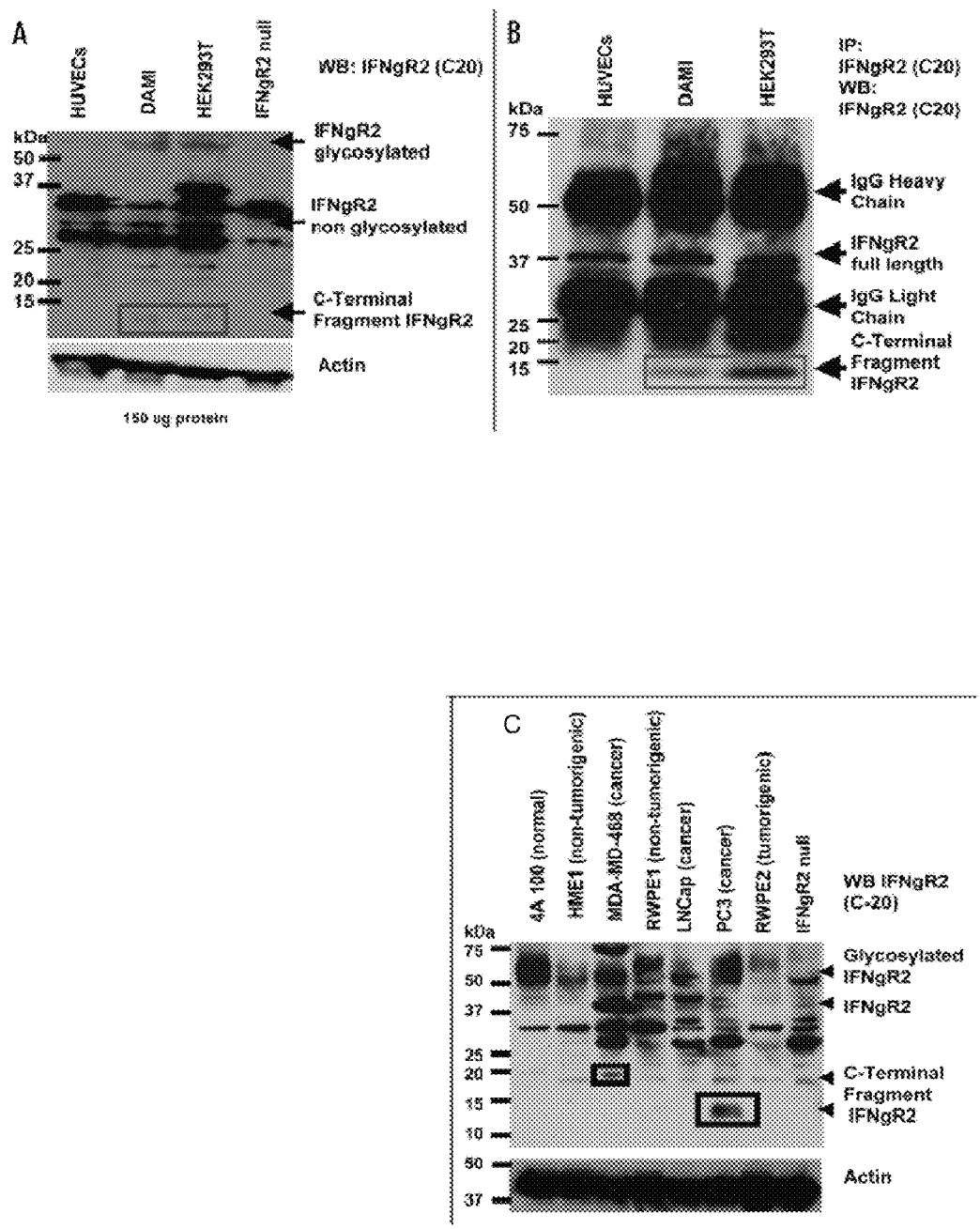
Figs. 9A-C

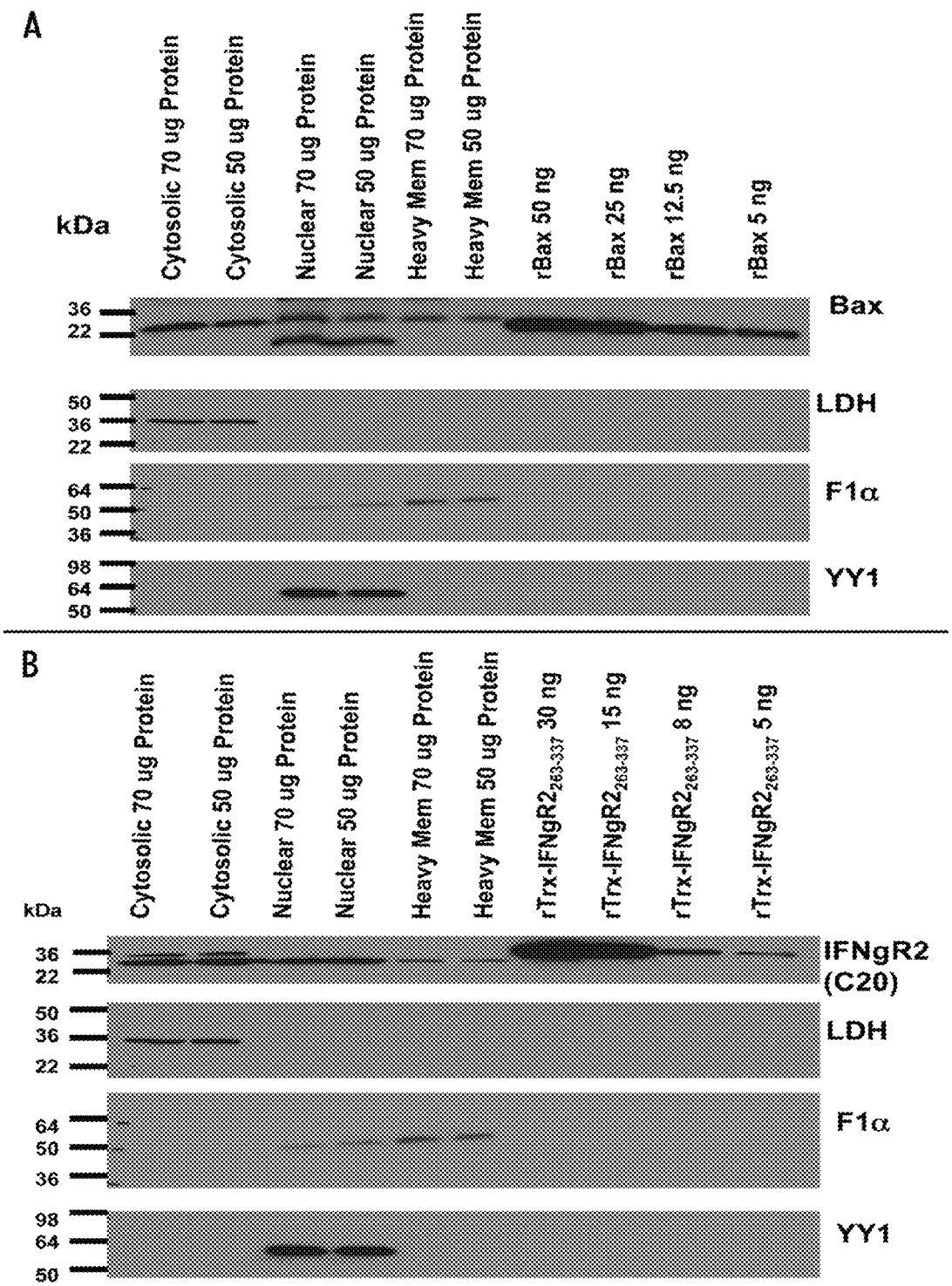
Fig. 10A-B

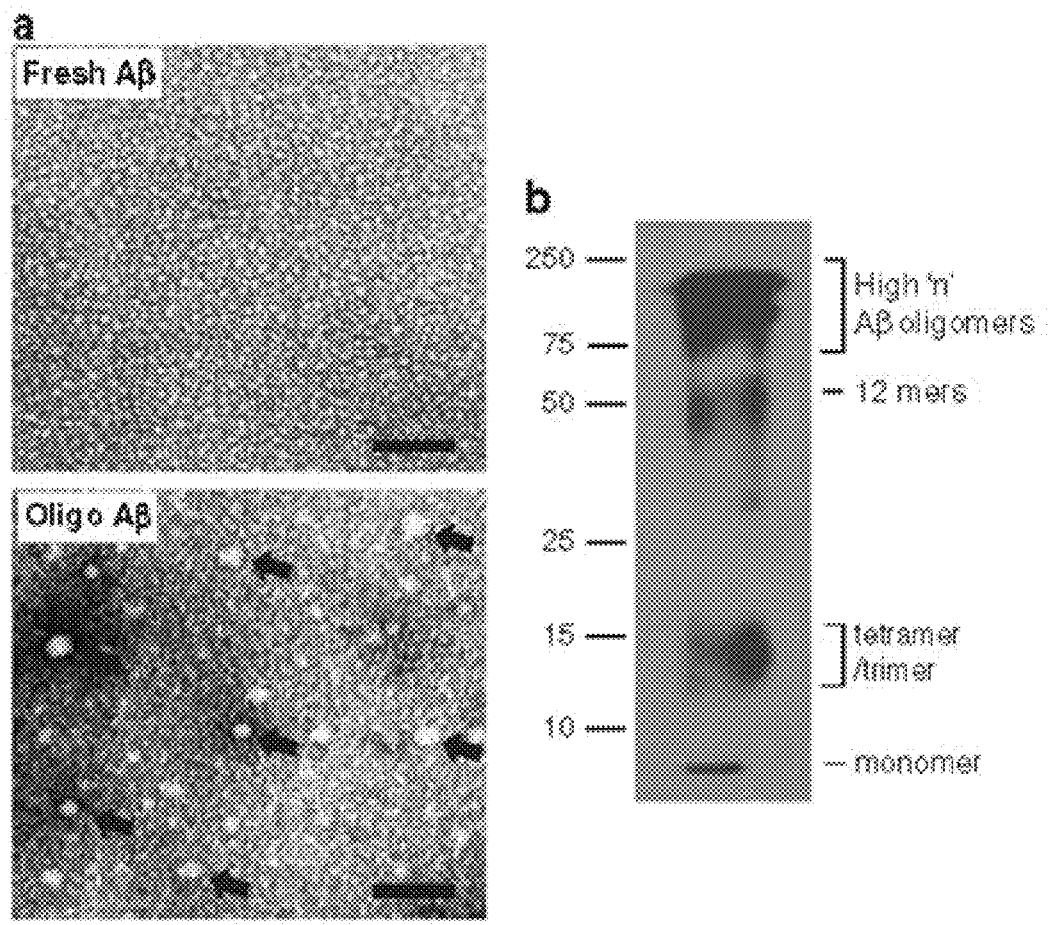
Figs. 11A-B

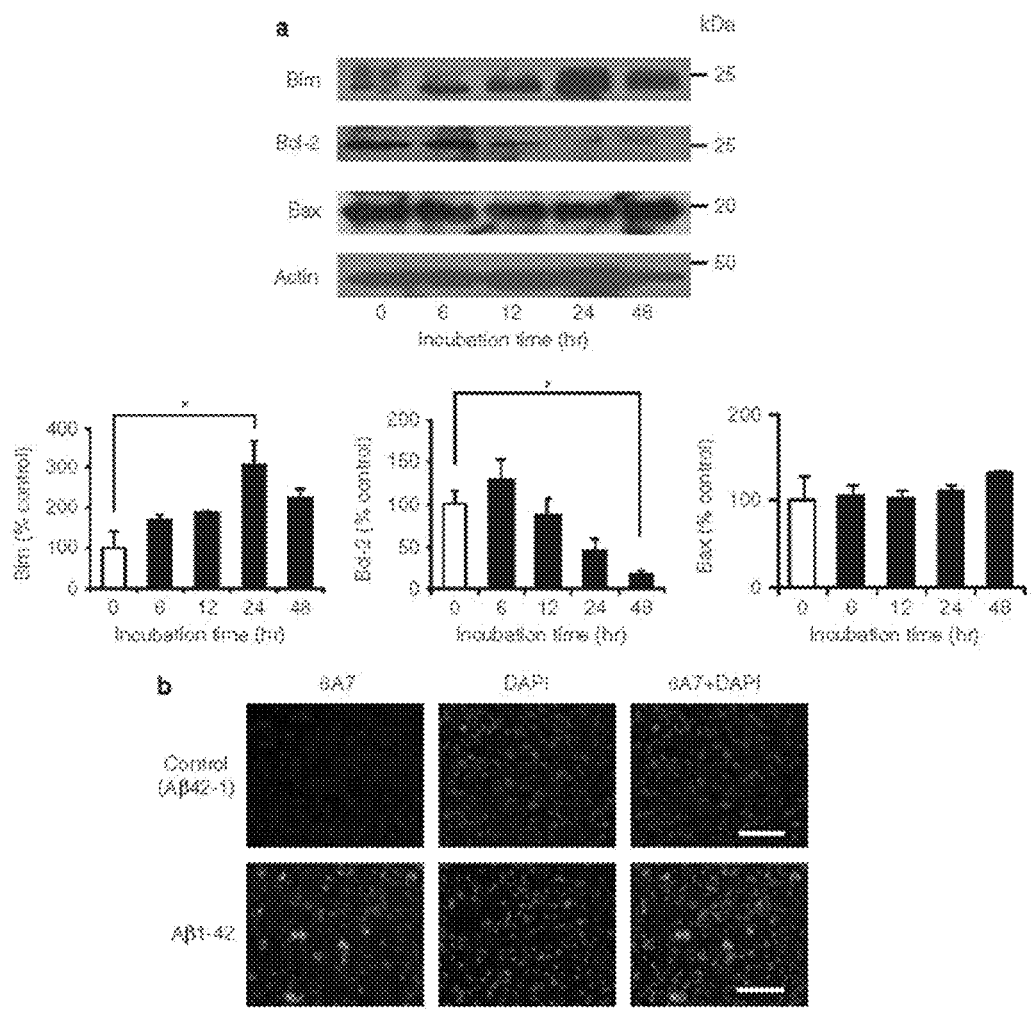
Figs. 12A-B

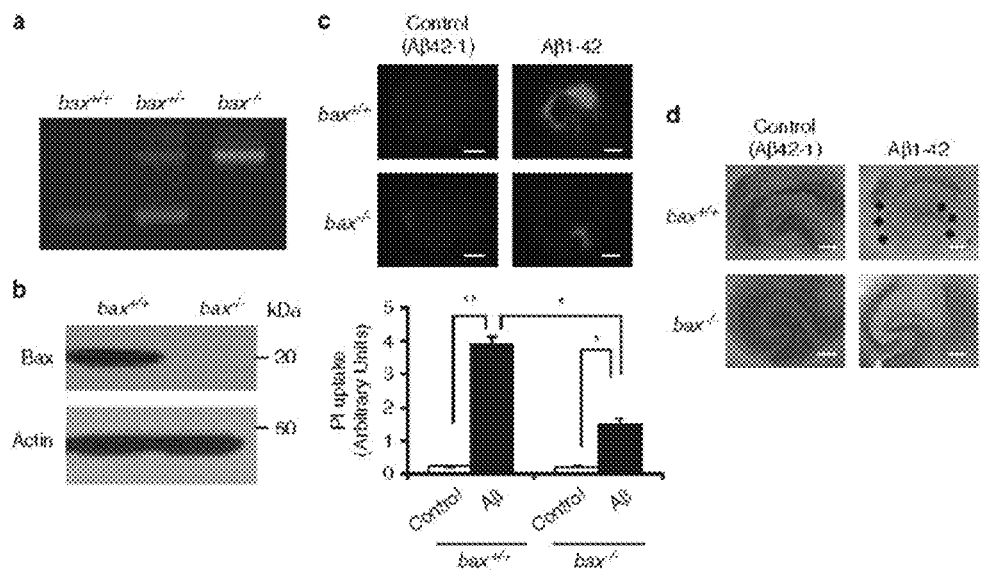
Figs. 13A-D
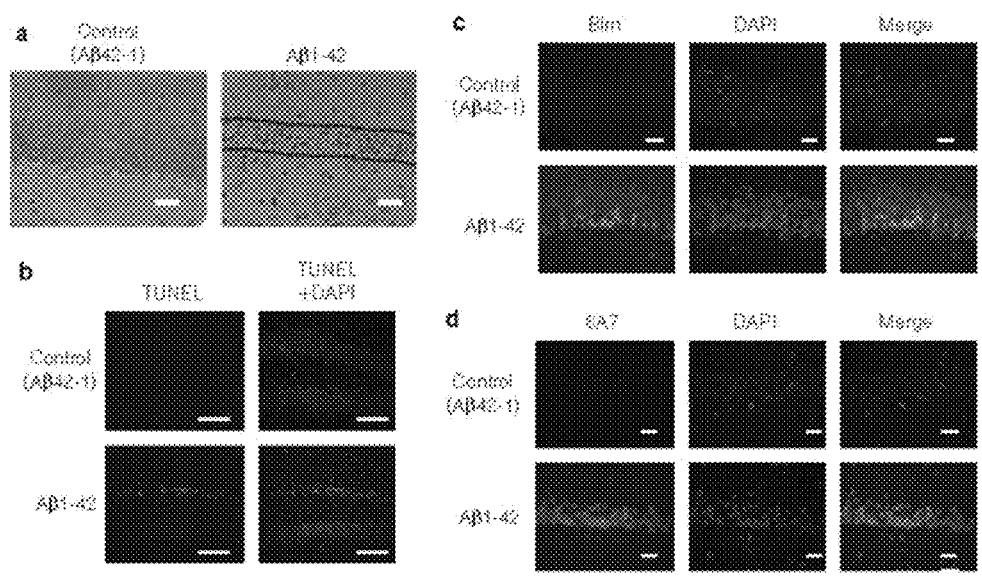
Figs. 14A-D

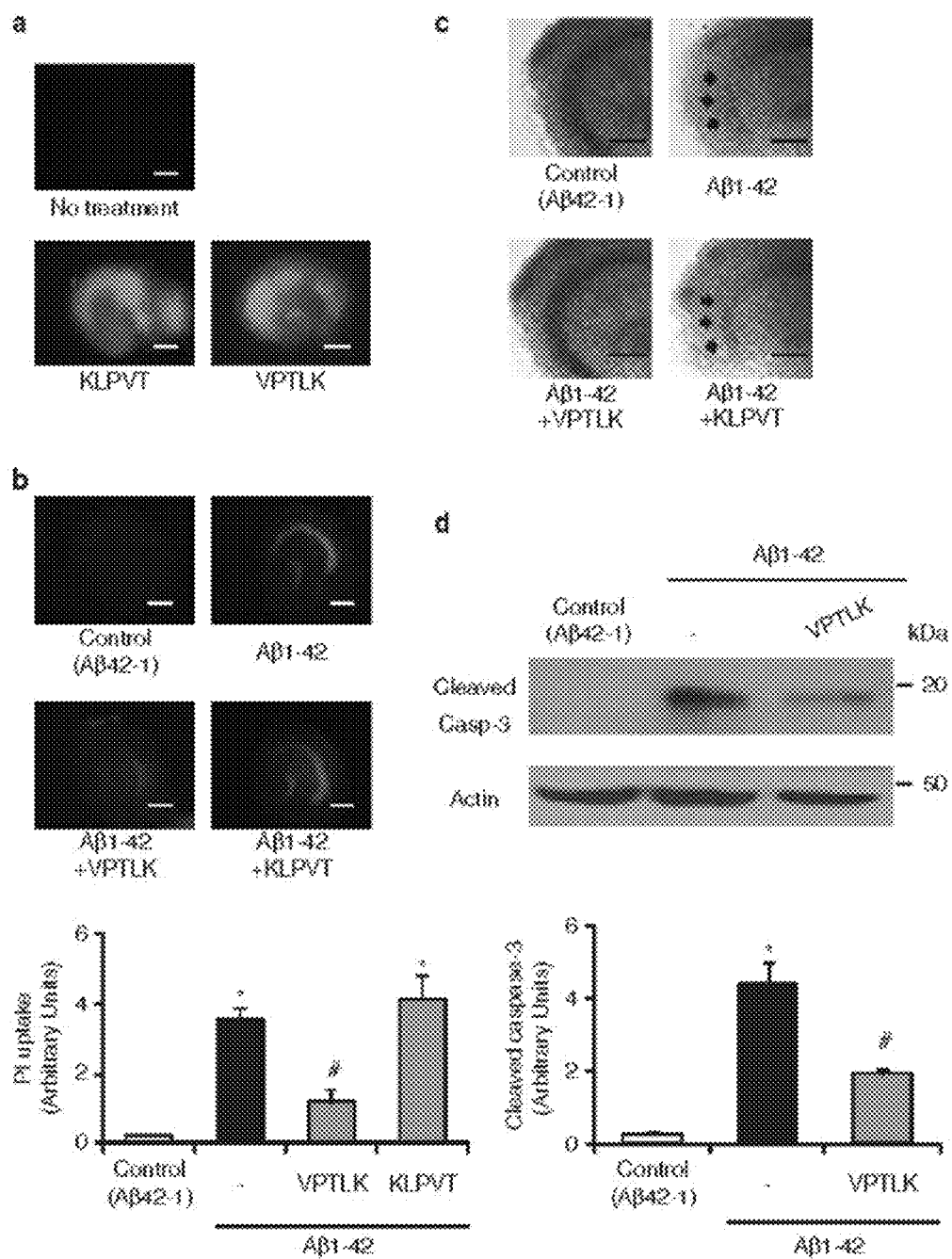
Figs. 15A-D ns # IFNγR2 COMPOSITIONS AND METHODS OF INHIBITING NEURONAL CELL DEATH

RELATED APPLICATION

This application is a Continuation-in-Part of U.S. patent application Ser. No. 13/679,439, filed Nov. 16, 2012, which is a Continuation of U.S. patent application Ser. No. 12/853,122, filed Aug. 9, 2010, Now U.S. Pat. No. 8,324,170, which claims priority to U.S. Provisional Application Ser. No. 61/232,050, filed Aug. 7, 2009, and claims priority from U.S. Provisional Application No. 61/824,437, filed May 17, 2013, the subject matter of which are incorporated herein by reference in their entirety.

BACKGROUND

The process of programmed cell death or apoptosis has been shown to be centrally involved in the pathogenesis of the significant majority of human illnesses and injury states. The cellular attrition observed in most degenerative conditions is apoptotic in nature; conversely, a failure of apoptosis has been proposed to underlie many forms of cancer. The central role of apoptosis in human disease clearly brings with it clinical promise; for example, the strong possibility exists that attenuation of apoptotic death will significantly modulate the severity of degenerative disorders.

Abnormal regulation of apoptosis is a cause of several diseases, including cancer and neurodegenerative disorders among others. Bax is a 21-kDa member of the conserved Bcl-2 family of proteins involved in regulating programmed cell death. Bax plays a key role in the intrinsic pathway of apoptosis. Bcl-2 family proteins are characterized by the presence of four Bcl-2 homology (BH) domains. Antiapoptotic members (e.g., Bcl-2, Bcl-XL and Mcl-1) have all four BH domains (BH1-4). The proapoptotic members are further divided into multi-domain proteins (e.g., Bax, Bak and Bok) containing three BH domains (BH 1-3) or BH3-only proteins (e.g., Bim, Bid and PUMA, etc.,) containing just the BH-3 domain. The molecular mechanisms, by which these proteins function and interact is not fully understood, but their role in apoptosis is indisputable. Although it has been extensively studied how Bcl-2 family proteins influence each other, it is not well known how these proteins are regulated by non-Bcl-2 family proteins.

SUMMARY

Embodiments described herein relate to a method of inhibiting β-amyloid (Aβ) induced neuronal cell death. The method includes administering to a neuronal cell exposed to a neurotoxic amount of Aβ a therapeutically effective amount of cell penetrating peptide (CPP). The CPP has an amino acid sequence that has at least 80% sequence identity to about 5 to about 41 consecutive amino acids of SEQ ID NO: 1.

In some embodiments, the CPP can have an amino acid sequence that has at least 90% sequence identity to about 5 to about 41 consecutive amino acids of SEQ ID NO: 1. For example, the CPP can have the amino acid sequence of SEQ ID NO: 1.

In other embodiments, the CPP can include the amino acid sequence of PILEA (SEQ ID NO: 2). The CPP can consist of about 5 to about 10 amino acids and include SEQ ID NO:2.

In still other embodiments, the neuronal cells can include neuronal cells of a subject with Alzheimer's disease.

In other embodiments, a Ku70-derived Bax-inhibiting peptide can be administered in combination with the CPP. The Ku70-derived Bax-inhibiting peptide can have the following formula: $X^1PX^2LX^3X^4$ (SEQ ID NO: 4), wherein $X^1$ is selected from amino acids with a non-polar side chain; $X^2$ is selected from amino acids with a non-polar side chain; $X^3$ is selected from amino acids with charged a polar side chain; $X^4$ is selected from amino acids with a charged polar side chain; and either $X^1$ or $X^4$ may be absent, although both may not be absent. The pharmaceutical composition further includes a pharmaceutical carrier. For example, the Ku70-derived Bax-inhibiting peptide can be selected from the group consisting of VPMLKE (SEQ ID NO:5), VPMLK (SEQ ID NO:6), PMLKE (SEQ ID NO:7), PMLK (SEQ ID NO:8), VPTLK (SEQ ID NO:9), and VPALR (SEQ ID NO:10).

BRIEF DESCRIPTION OF DRAWINGS

FIG. 1 illustrates that IFNγR2 cytoplasmic domain inhibits Bax-induced cell death. (A) The C-terminus (amino acids 263-337) of interferon gamma receptor beta chain (IFNγR2) was cloned as a Bax suppressor in a yeast-based functional screen for Bax inhibitors. The image shows rescue of yeast growth from Bax expression by IFNγR2 (amino acids 263-337) and Ku70 (served as a positive control). (B) Schematic representation of IFNγR2 wild-type (w.t.) protein and its truncated forms used in this study.

FIG. 2 illustrates that IFNγR2 protects cells from Bax-induced cell death independent of the Jak2-signaling pathway. (A) The IFNγR2 C-terminal region (296-337) inhibited apoptosis induced by Bax overexpression. HEK293 cells were transiently co-transfected with pcDNA3-h Bax and pEGFP C2-IFNγR2wild type, -IFNγR2$_{1-295}$ or -IFNγR2$_{296-337}$, and apoptosis was determined 24 h after the transfection, as described in the Materials and Methods section. Each bar represents the mean of triplicate samples and standard errors, and statistical significance was determined by an unpaired student t test: ***p<0.001. (B) Plasmid-mediated expression of IFNγR2 inhibited etoposide-induced apoptosis in IFNγR2 null cells. IFNγR2 null cells were transiently transfected (see Materials and Methods) with pEGFP-C2-IFNγR2wild type, -IFNγR2$_{1-295}$ or -IFNγR2$_{296-337}$. One day after the transfection, cells were treated with 10 μM etoposide for 24 h, and apoptosis was detected by using Hoechst nuclear staining. Each bar represents the mean of triplicate samples and standard errors, and statistical significance was determined by an unpaired student t test: *p<0.05, and *p<0.001. (C) Plasmid-mediated expression of IFNγR2 inhibited etoposide-induced Caspase 3 activation in IFNγR2 null cells. IFNγR2 null cells were transiently transfected (see Materials and Methods) with pEGFP-C2-IFNγR2wild type, -IFNγR2$_{1-295}$ or -IFNγR2$_{296-337}$. One day after transfection, the cells were treated with 10 μM etoposide for 24 h. Caspase 3 activity was measured as described in the Materials and Methods section. Each bar represents the mean of triplicate samples and standard errors, and statistical significance was determined by an unpaired student t test: *p<0.001. (D and E) Bax inhibition by IFNγR2 is independent of Jak2. (D) Jak2 null cells were transiently transfected with pEGFP-C2-IFNγR2wild type, -IFNγR2$_{1-295}$ or -IFNγR2$_{296-337}$. One day after the transfection, the cells were treated with 10 μM etoposide for 24 h. Apoptosis was detected by using Hoechst nuclear staining as described in the Materials and Methods section. Each bar represents the mean of triplicate samples and standard errors, and statistical significance was determined by an unpaired student t test: *p<0.001. (E) Jak2 null cells were transiently transfected with pEGFP-C2-IFNγR2wild type, -IFNγR2$_{1-295}$ or -IFNγR2$_{296-337}$. One day after transfection the cells were treated with etoposide 10 μM for 24 h. Caspase 3 activity was measured as described in the Materials and Methods section. Each bar represents the mean of triplicate samples and standard errors, and statistical significance was determined by an unpaired student t test: *p<0.001.

FIG. 3 illustrates that IFNγR2 knock-down sensitizes HeLa cells to apoptosis. (A) IFNγR2 shRNA was expressed in HeLa cells from a lentivirus vector. For control shRNA, non-IFNγR2-targeted shRNA (targeting GFP), and empty vector were used. IFNγR2 expression levels were analyzed by western blotting using IFNγR2C-20 antibody (Santa Cruz). Actin was used for a loading control. (B) HeLa cells expressing shRNA against IFNγR2 were treated with 10 μM etoposide for 24 h. Apoptosis was detected by Hoechst dye nuclear staining as described in the Materials and Methods section. Each bar represents the mean of triplicate samples and standard errors, and statistical significance was determined by an unpaired student t test: ***p<0.001.

FIG. 4 illustrates that IFNγR2C-terminus inhibits Bim-induced apoptosis but not Bak-induced apoptosis. (A) IFNγR2 inhibited Bim-induced apoptosis in HEK293T cells. HEK293T cells were transiently co-transfected with pcDNA3-h Bim EL and pEGFP-C2-IFNγR2wild type, -IFNγR2$_{1-295}$ or IFNγR2$_{296-337}$ as described in Materials and Methods. Apoptosis induction was analyzed 24 h after the transfection by using Hoechst dye nuclear staining. Each bar represents the mean of triplicate samples and standard errors, and statistical significance was determined by an unpaired student t test: ***p<0.001. (B) IFNγR2 did not inhibit Bak-induced apoptosis. HEK293 cells were transiently co-transfected (see Materials and Methods) with pcDNA3-h Bak and pEGFP-C2-IFNγR2wild type, -IFNγR2$_{1-295}$ or —IFNγR2$_{296-337}$, and apoptosis induction was analyzed 24 h after the transfection. Each bar represents the mean of triplicate samples and standard errors.

FIG. 5 illustrates that localization of IFNγR2. HeLa and HEK293 cells were transfected with pEGFP-C2 IFNγR2wild type, pEGFP-C2-IFNγR2$_{1-295}$ or pEGFP-C2-IFNγR2$_{296-337}$. One day after the transfection, the subcellular locations of the IFNγR2-EGFP fusion proteins were determined by fluorescence microscopy. (A and B) HeLa cells transfected with pEGFP vector. (C and D) HeLa cells transfected with pEGFP-C2-IFNγR2wild type. (E and F) HeLa cells transfected with pEGFP-C2-IFNγR2$_{296-337}$. (G and H) HeLa cells transfected with pEGFP-C2-IFNγR2$_{1-295}$. (I) HEK293 cells transfected with pEGFP-C2-IFNγR2wild type. (J) Mito-tracker staining of HE293 cells transfected with pEGFP-C2-IFNγR2 wild type as in (I). Images are 40× magnification. (K) The percentages of cells showing a punctuate pattern of GFP signals (mitochondrion-like distribution) in each group are presented in K. Each bar represents the mean of triplicate samples and standard errors.

FIG. 6 illustrates a Western blot analysis of EGFP-tagged IFNγR2 proteins (A) Expression of IFNγR2 EGFP fusion proteins in IFNγR2 null (mutant HT1080) cells after the transient transfection. Cells were transfected with pEGFP-C2-IFNγR2 wild type, pEGFP-C2-IFNγR2$_{1-295}$ or pEGFP C2-IFNγR2$_{296-337}$. One day after the transfection, the cells were collected for western blot analysis with anti-EGFP polyclonal antibody (Abcam). IFNγR2-GFP fusion proteins were detected as bands with the expected molecular weights. However, smaller forms, probably resulting from protease-dependent cleavage, were also detected (* indicates a cleaved form of IFNγR2-GFP fusion proteins). (B) Western blot analysis of IFNγR2-GFP fusion proteins in HEK293 cells. Cells were transfected with pEGFP-C2-IFNγR2wild type, pEGFP-C2-IFNγR2$_{1-295}$ or pEGFP-C2-IFNγR2$_{296-337}$. One day after the transfection, cells were collected for western blot analysis using EGFP polyclonal antibody (Abcam). Although intact (non-cleaved) GFP-IFNγR2$_{296-337}$ was detected, intact IFNγR2wild type-GFP and IFNγR2$_{1-295}$-GFP were not detected. Instead, cleaved forms of these proteins were observed (* indicates these cleaved forms). (C and D) Confirmation of expression of IFNγR2-GFP fusion proteins by enrichment of the fusion proteins using immunoprecipitation. One day after the transfection of pEGFP-C2-IFNγR2wild type (C), pEGFP-C2-IFNγR2$_{1-295}$ (C), or pEGFP-C2-IFNγR2$_{296-337}$ (D), HEK293 cells were collected and immunoprecipitation was performed by using anti-GFP polyclonal antibody (Abcam). The samples were subjected to western blot analysis using anti IFNγR2 detecting the N-terminal portion of IFNγR2 as an epitope (IFNγR2 antibody from Fitzgerald) (C) or anti-IFNγR2 detecting the C-terminal 20 amino acids of IFNγR2 (IFNγR2 C20 antibody from Santa Cruz) (D). Intact fusion proteins were detected as bands with the expected molecular weights (approximately 67 kDa in (C) and 34 kDa in (D)). In the "Input" lanes of (C), the strong background staining prevented the detection of both endogenous IFNγR2 and INFγR2-GFP fusion proteins. In the "Input" lanes of (D), endogenous IFNγR2 as well as fusion protein were detected by anti-IFNγR2 antibody. Seven hundred micrograms of total protein were used in the IP experiments, and 150 μg of total protein was used for input level.

FIG. 7 illustrates that the C-terminal portion of IFNγR2 (amino acids 296-337) is sufficient to inhibit Bax activation. HeLa cells were transfected with pEGFP-C2 vector (A), pEGFP-C2-IFNγR2$_{1-295}$ (B), -IFNγR2$_{296-337}$ (C) or -IFNγR2wild type (D) as described in Materials and Methods. After 24 h of transfection, the cells were treated with staurosporine 100 nM for 3 h. Then, the cells were washed with phosphate buffer pH 7.4 (PBS), fixed by paraformaldehyde 1%, permeabilized with Triton X-100 (0.02%), blocked with goat serum, and the activation of Bax was analyzed by immunostaining with anti-Bax 6A7 monoclonal antibody (which recognizes active Bax). Arrowheads indicate cells both positive for GFP and active Bax (Bax 6A7+ cells). Images are at 20× magnification. (E) Percentages of cells that were stained by Bax 6A7 Ab among GFP positive cells are shown. Each bar represents the mean of triplicate samples and standard errors, and statistical significance was determined by an unpaired student t test: ***p<0.001.

FIG. 8 illustrates that IFNγR2 interacts with Bax. (A and B) Co-immunoprecipitation of endogenous IFNγR2 and Bax. HEK293T cells were lysed using CHAPS or NP40 buffer as described in Materials and Methods. Immunoprecipitation (IP) was performed in the same buffer (NP40 or CHAPS) with an anti-Bax polyclonal (A) or an anti-IFNγR2 mouse monoclonal antibody (B). (A) HEK293T cell lysates were prepared in CHAPS or NP40 buffer. IP and western blot (WB) were performed with anti-Bax polyclonal (BD Pharmingen) and anti-IFNγR2 monoclonal (Fitzgerald) antibodies, respectively. (B) HEK293T cells were lysed with NP40 buffer, IP and WB were performed with anti-IFNγR2 monoclonal (Fitzgerald) and anti-Bax polyclonal (N20), respectively. (C) Bax inhibiting peptide (BIP) derived from Ku70 (VPTLK) did not compete with IFNγR2 to bind Bax. HEK 293T cells were lysed in CHAPS buffer, and BIP was added to the cell lysate to examine its effect on the interaction of Bax and IFNγR2 as described in Materials and Methods. Co-immunoprecipitation was performed with anti-IFNγR2 monoclonal antibody (Fitzgerald), and western blotting was done using anti-Bax N20 polyclonal antibody (Santa Cruz).

FIG. 9 illustrates the detection of the C-terminal fragment of IFNγR2 in transformed cells. (A) western blot analysis of IFNγR2 in DAMI (human megakaryoblast cell line), HEK293T (SV40 Large T-transformed cell line), and HUVEC (non-transformed cells). Total cell lysates (150 μg protein/lane) were analyzed. INFγR2 null cells were used as a negative control sample to distinguish specific bands from nonspecific bands (A, right lane). (B) Enrichment of the C terminal fragment by immunoprecipitation (IP). Cells (HUVEC, DAMI and HEK293T cells) were lysed using RIPA buffer. Both IP and WB were performed with anti-IFNγR2 (C20, Santa Cruz) polyclonal antibody. The C-terminal fragment of IFNγR2 was detected in DAMI and HEK293T cells, but not in HUVEC. (C) Western blot analysis of IFNγR2 in various human cell types: human normal mammary epithelial cell line (4A100), non-tumorigenic immortalized breast cell line (HME1), tumorigenic human breast cancer cell line (MDAMD 468), non-tumorigenic (RWPE1) and tumorigenic (RWPE2) human prostate cell lines, and tumorigenic human prostate cancer cell lines (LNCap and PC3). INFγR2 null cells were used as a negative control to distinguish specific bands from non-specific bands detected with the IFNγR2C20 antibody.

FIG. 10 illustrates the measurement of cellular concentrations of IFNγR2 and Bax. Purified recombinant proteins of rTrx-IFNγR2$_{263\text{-}337}$ and Bax (ΔTM) were used as standards. DAMI cells were lysed in hypotonic buffer supplemented with protease inhibitors. Each subcellular fraction from equivalent cell numbers, and sequential dilutions of protein standards were subjected to SDS-PAGE, and transferred to nitrocellulose membrane. Bax-N20-HRP antibody (Santa Cruz) and IFNγR2C-20 antibody (Santa Cruz) were used to detect Bax (A) and IFNγR2 (B), respectively. Signal intensities were analyzed by using BioRad Gel Doc and Quantity One 4.5.1 software from BioRad. LDH, F1α and YY1 were used as cytosolic, mitochondrial and nuclear markers, respectively.

FIG. 11 illustrates physicochemical and morphological features of the synthetic Aβ$_{1\text{-}42}$. (a) Electron micrograph shows the typical pattern of oligomer formation of Ab. The arrows indicate oligomers in the lower panel. Scale bar, 100 μm. (b) Synthetic Aβ$_{1\text{-}42}$ was subjected to SDS-polyacrylamide gel and detected by western blotting with 6E10 antibody. Molecular weight markers in kDa are at left.

FIG. 12 illustrates oligomeric Aβ differentially regulates Bim, Bcl-2 and Bax in the hippocampal slice culture. (a) Representative western blots showed oligomeric Aβ induced upregulation of Bim and downregulation of Bcl-2 in a time-dependent manner. Bax levels were not changed by oligomeric Aβ treatment. Actin was used as internal loading control. The values of each band were normalized to that of actin and shown as a relative value of each group compared with the non-treatment slices. The indicated comparisons are significant at *P<0.05, n=4. (b) Immunocytochemistry analysis demonstrated the increased number of positive cells stained with 6A7 antibody, which specifically detect the active form of Bax, 24 h after oligomeric Aβ treatment in hippocampal slice cultures. Conversely, control peptide (Aβ$_{42\text{-}1}$) did not induce the active form of Bax (green: 6A7, blue: DAPI). Scale bar, 100 μm.

FIG. 13 illustrates bax$^{-/-}$ neurons are resistant to oligomeric Aβ neurotoxicity. (a) DNA was extracted from bax$^{+/+}$ and bax$^{-/-}$ mice, and each genotype was identified by PCR with the primer sets specifically detecting each genotype as described in the previous study. Bax$^{+/+}$ yields a 304-bp PCR product and bax$^{-/-}$ yields a 507-bp PCR product. (b) Total protein (20 μg) from whole brain was analyzed by immunoblot with anti-Bax antibody. Immunoblot analysis showed Bax in bax$^{+/+}$ mouse samples at the expected molecular weight of 20 kDa, and no expression of Bax in bax$^{-/-}$ samples. (c) Hippocampal slice culture were treated with oligomeric Aβ (500 nM) in the presence of PI (red) for 48 h. Representative data showed oligomeric Aβ-induced PI uptake was significantly reduced in the slice cultures from bax$^{-/-}$ mice compared with bax$^{+/+}$ mice. The PI uptake was quantitatively analyzed (n=5). Control Aβ$_{42\text{-}1}$ peptide had no effect on PI uptake. Scale bar, 500 μm. *P<0.05. (d) Neuronal cell loss by oligomeric Aβ (arrows) was significantly reduced in the hippocampal slice cultures from bax$^{-/-}$ mice. Scale bar, 500 μm.

FIG. 14 illustrates intrahippocampal injection of oligomeric Aβ upregulates Bim and activates Bax. C57BL/6J mice were killed and the levels of Bim and active Bax were analyzed at 10 or 20 days after oligomeric Aβ injection. (a) At 20 days after oligomeric Aβ injection, neuronal cell loss in hippocampus was evident in Aβ injected mice in H&E staining, but not in control peptide-injected mice. The region of neuronal cell loss is indicated by dotted lines. Scale bar, 100 μm. (b) The number of TUNEL-positive cells in hippocampus was dramatically increased after oligomeric Aβ injection whereas virtually no TUNEL-positive cell (green) was detected in control peptide-injected hippocampus tissues. Blue:DAPI. Scale bar, 200 mm. (c) Immunoreactivity for Bim (green) was increased in hippocampus at 10 days after the oligomeric Aβ injection. Scale bar, 100 mm. (d) The number of active Bax-positive cells detected by 6A7 antibody (red) was dramatically increased at 10 days after the oligomeric Aβ injection. Scale bar, 100 mm compared with control peptide-injected mice.

FIG. 15 illustrates Bax-inhibiting peptide (BIP) suppresses neuronal cell death induced by oligomeric Ab. Either BIP (VPTLK) or control peptide (KLPVT) was added to hippocampal slice cultures at the same time with oligomeric Aβ to examine its neuroprotective effect. (a) Cell permeability of both peptides was confirmed by green fluorescence in hippocampal slice cultures. Strong green fluorescence of both BIP- and negative-control peptide was found at 24 h after the peptide treatment, indicating both peptides are penetrated to neurons. (b) The intensity of PI in slices treated with oligomeric Aβ for 48 h was quantified as a marker of cell death. BIP significantly prevented oligomeric Aβ-induced PI uptake (n=5). Scale bar, 500 μm. *P<0.01 versus control #P<0.05 versus *P<0.05 only (−). Aβ$_{42\text{-}1}$ peptide was used as a control. (c) Niss1 staining demonstrated that the treatment of BIP significantly prevented neuronal cell loss induced by oligomeric Aβ. Arrows indicate the region of neuronal cell loss. (d) BIP suppressed the activation of caspase-3 (cleaved caspase-3) induced by oligomeric Aβ (n=4). **P<0.01 versus control, #P<0.05 versus Aβ only (−).

DETAILED DESCRIPTION

Figure 16:
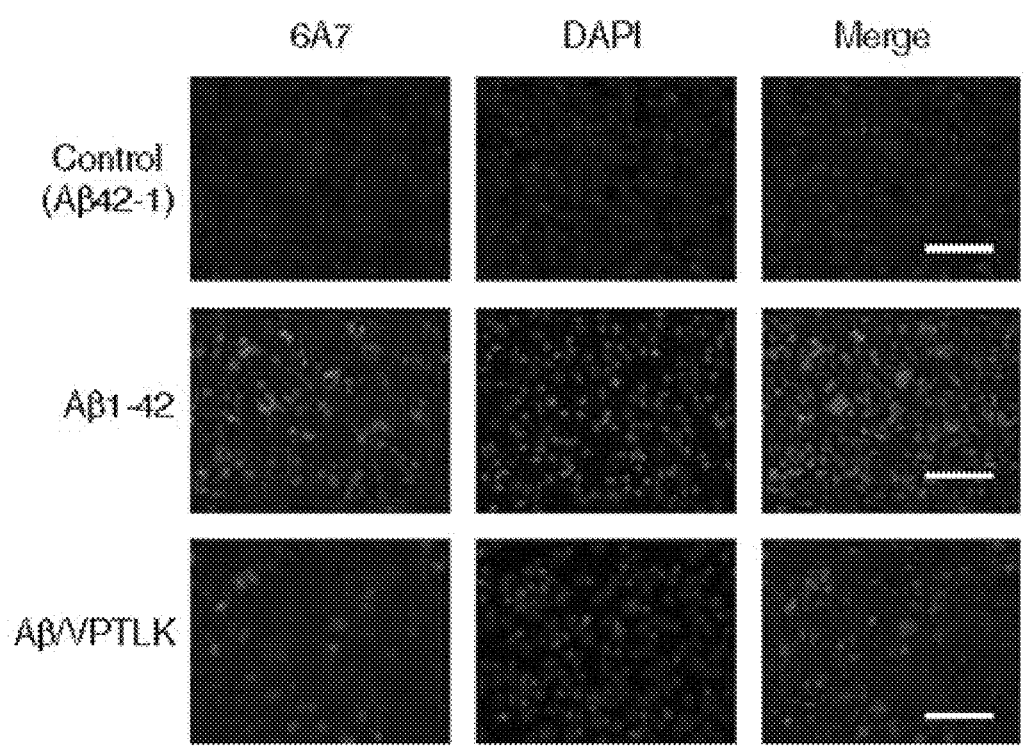
FIG. 16 illustrates BIP prevents the conformational change of Bax induced by oligomeric Aβ. BIP (VPTLK) was used to treat hippocampal slice cultures with oligomeric Aβ for 48 h. Aβ42-1 was used as a control. The slices were stained with 6A7 antibody for detecting active conformational change of Bax. In the BIP-treated slices, the number and intensity of 6A7-positive signal (green) was significantly decreased compared with the slices treated with Aβ only. Scale bar, 100 mm.

Embodiments described herein relate to a method of inhibiting or mitigating apoptosis in a cell and particularly relates to a method of inhibiting β-amyloid (Aβ) induced neuronal cell death. It was found that the cytoplasmic domain (or C-terminal domain) of the interferon gamma receptor beta chain (IFNγR2) acts as a novel Bax suppressor in mammalian cells. Bax is a well-known pro-apoptotic protein that mediates intrinsic cell-death signaling. The C-terminal domain of IFNγR2 can be used to design cell penetrating peptides (CPPs) that can inhibit the activation of Bax in human cell lines, thereby inhibiting Bax mediated apoptosis of the cells. CPPs in accordance with one aspect of the present invention that can inhibit activation of Bax in human cells can have an amino acid sequence substantially homologous to a portion of the C-terminal region (SEQ ID NO:1) of the C-terminus of IFNγR2 (IFNγR2$_{296-337}$).

CPPs derived from or based on the amino acid sequence of the C-terminus of IFNγR2 do not contain the Jak2-binding domain; and therefore, the anti-apoptotic function of IFNγR2 is independent of JAK/STAT signaling. CPPs derived from or based on the C-terminus of IFNγR2 can also rescue human cells from apoptosis induced by overexpression of Bax but not Bak. By way of example, CPPs derived from or based on the amino acid sequence of the C-terminus of IFNγR2 can rescue Bim induced apoptosis (Bax mediated) (FIG. 4A), but not rescue cells from apoptosis induced by Bak mediated apoptosis (FIG. 4B).

CPPs derived from or based on the amino acid sequence of the C-terminus of IFNγR2 can bind to both inactive Bax and active N-terminus exposed Bax molecules. Bax activation involves exposure of the protein's N-terminus by a conformational change followed by Bax translocation from the cytosol to mitochondria (Li et al., Cell Death Differ 2007, Nechushtan et al., EMBO J, 1999; 18:2330-41; Wolter et al., J Cell Biol 139:1281-92, 1997). The Example below shows that IFNγR2 is able to bind to the active exposed N-terminus Bax molecules and inhibits the conformational change and mitochondrial translocation of Bax (FIG. 7). The Example below further illustrates that IFNγR2 interacts with Bax in a detergent-free buffer (CHAPS) that maintains the inactive conformation of Bax (FIG. 8), indicating that the inventive CPPs bind to and inhibit inactive Bax.

In some embodiments, a method of inhibiting β-amyloid (Aβ) induced neuronal cell death includes administering to a neuronal cell exposed to a neurotoxic amount of Aβ a therapeutically effective amount of cell penetrating peptide (CPP). The CPP can consist of about 5 to about 41 amino acids and be substantially homologous or have an at least about 80%, about 90%, or about 95% sequence identity to about 5 to about 41 consecutive amino acids of a portion of the amino acid sequence of the C-terminal region of interferon gamma receptor 2 (IFNγR2). An "effective amount" or "therapeutically effective amount" of CPP administered to a cell is the amount of the CPP effective to mitigate Bax mediated apoptosis in the cell. In some embodiments, the Bax mediated apoptosis is induced by cytotoxic stresses elicited from chemo- and radiotherapy delivered to the cell.

In one embodiment of the invention, the CPP can have an amino acid sequence substantially homologous to the amino acid sequence of SEQ ID NO: 1. By "substantially homologous" to the amino acid sequence of SEQ ID NO: 1 it is meant that the CPP can be a fragment, analog or derivative of mammalian SEQ ID NO: 1 that differs from the amino acid sequence of SEQ ID NO: 1 in one or more amino acids. The amino sequence of such CPPs can feature a deletion, addition, or substitution of one or more amino acids of SEQ ID NO: 1. Amino acid insertions are preferably of about 1 to 4 contiguous amino acids, and deletions are preferably of about 1 to 10 contiguous amino acids. CPP fragments substantially homologous to the amino acid sequence of SEQ ID NO: 1 can substantially maintain the CPPs functional activity of inhibiting Bax mediated apoptosis in cells. In one example, a CPP having an amino acid sequence substantially homologous to SEQ ID NO:1 can have an amino acid sequence that has at least about 80%, 90%, about 95%, or about 99% sequence identity to about 5 about 41 consecutive amino acids of SEQ ID NO: 1.

CPP Bax inhibiting fragments of the amino acid sequence of SEQ ID NO: 1 can be obtained by screening peptides recombinantly produced or chemically synthesized and tested for Bax inhibiting activity. For example, a CPP fragment of a peptide having an amino acid sequence of SEQ ID NO: 1 may be arbitrarily divided into fragments of desired length with no overlap of the fragments, or preferably divided into overlapping fragments of a desired length. The fragments can be produced and tested to identify those peptidyl fragments, which can function as Bax inhibiting peptides.

In some embodiments, the CPP can be a peptide of about 5 to about 10 amino acids in length and include each of the individual amino acids of SEQ ID NO:2 (PILEA). It is further contemplated that each of the individual amino acids of SEQ ID NO:2 can be included in such a peptide at any position relative to each other. In one particular embodiment of the invention, a five amino acid peptide corresponding to SEQ ID NO:2, has cell penetration activity and upon administration to the cell is sufficient to inhibit Bax mediated apoptosis.

The five amino acid peptide of SEQ ID NO:2, as well as variants and modified peptides (e.g., modified for better membrane permeablization or longer stability) are also cell penetrating peptides, and may be used to protect cells from apoptosis in accordance with the present invention. For example, CPPs of the present invention may further include peptides with slight modifications (e.g., substitution of similar charged amino acids or addition of 1, 2 or 3 innocuous amino acids at either end or by the addition of an innocuous entity or moiety) to the peptide sequences described herein. By "innocuous", it is meant that the amino acid(s) or entities do not substantially reduce the Bax-inhibiting activity of the core peptide sequence PILEA (SEQ ID NO: 2). Therefore, in some embodiments, a composition comprising a Bax-inhibiting peptide of the present invention includes a peptide described herein (e.g., PILEA (SEQ ID NO: 2)), with additions of 1, 2 or 3 innocuous amino acids at either end and/or innocuous amino acid substitutions. The present invention can also include peptides in which sequences described above are repeated multiple times.

However, peptide delivery and therapeutic administration may be limited by permeability and selectivity problems involving the cell membrane (Morris et al., Nat. Biotechnology. 19 (12):1173-1176, 2001). Therefore, in some embodiments CPPs can further include the addition of small protein domains called protein transduction domains (PTD's) to either end of the peptide. PTD's can aid in either the transport of CPPs to specific target cells or to aid the stability of the molecule as they have been shown to cross biological membranes and act independently from transporters or specific receptors to promote delivery of peptides into cells (see Hawiger, Curr. Opin. Chem. Biol. 3 (1):88-94, 1999).

A CPP of the present invention may be administered to a cell, such a neuronal cell, in any manner known in the art, which allows for the delivery of the CPP inside the cell. In some embodiments, there is no need to use a delivery tool, such as a liposome to administer a CPP to a cell given the cell penetrating property of the peptide. One example of a method of administering a CPP to a cell is to add an effective amount of CPP directly into culture media to protect cells from cytotoxic stresses.

In some embodiments of the invention, an additional membrane permeable peptide, which inhibits Bax-mediated apoptosis, may be co-administered to a cell with the inventive CPPs described above. In some particular embodiments, the co-administered peptide includes Ku-70 derived Bax-inhibiting peptides (BIPs). These BIPs are described in U.S. Pat. No. 7,314,866 B2, which is incorporated herein by reference.

A BIP for use in the present invention can include VPMLKE (SEQ ID NO: 5), VPMLK (SEQ ID NO: 6), PMLKE (SEQ ID NO: 7), PMLK (SEQ ID NO: 8), VPTLK (SEQ ID NO: 9), or VPALR (SEQ ID NO: 10). Advantageously VPMLK (SEQ ID NO:6), PMLKE (SEQ ID NO:7), PMLK (SEQ ID NO:8), VPTLK (SEQ ID NO:9), and VPALR (SEQ ID NO:10) are also cell membrane permeable and do not require a cell delivery system, such as liposomes.

In another particular embodiment, a BIP for use in the methods of the present invention includes a peptide of the general formula $X^1PX^2LX^3X^4$ (SEQ ID NO:4), wherein:

$X^1$=Amino acids with a non-polar side chain, such as Glycine (G), Alanine (A), Valine (V), Leucine (L), Isoleucine (I), Methionine (M), Proline (P), Phenylalanine (F), or Tryptophan (W).

$X^2$=Amino acids with a non-polar side chain, such as Glycine (G), Alanine (A), Valine (V), Leucine (L), Isoleucine (I), Methionine (M), Proline (P), Phenylalanine (F), Tryptophan (W) or Threonine (T).

$X^3$=Amino acids with a charged polar side chain, such as Lysine (K), Arginine (R), Histidine (H), Aspartic acid (D), Glutamic acid (E), and $X^4$=Amino acids with a charged polar side chain, such as Lysine (K), Arginine (R), Histidine (H), Aspartic acid (D), Glutamic acid (E).

Either $X^1$ or $X^4$ may be absent.

The present invention also relates to a pharmaceutical composition comprising a CPP as described above. A pharmaceutical composition in accordance with invention can further include a BIP as described above and/or a suitable pharmaceutical carrier. In one exemplary embodiment, the pharmaceutical composition includes a five amino acid long peptide of SEQ ID NO:2, a BIP selected from the group consisting of the VPMLKE (SEQ ID NO:5), VPMLK (SEQ ID NO:6), PMLKE (SEQ ID NO:7), PMLK (SEQ ID NO:8), VPTLK (SEQ ID NO:9), and VPALR (SEQ ID NO:10), and a pharmaceutical carrier.

In another exemplary embodiment, the pharmaceutical composition includes a five amino acid long peptide of SEQ ID NO:2, a BIP having the following formula: $X^1PX^2LX^3X^4$ (SEQ ID NO: 4), wherein $X^1$ is selected from amino acids with a non-polar side chain; $X^2$ is selected from amino acids with a non-polar side chain; $X^3$ is selected from amino acids with a charged polar side chain; $X^4$ is selected from amino acids with a charged polar side chain; and either $X^1$ or $X^4$ may be absent, although both may not be absent, and a pharmaceutical carrier.

The pharmaceutical compositions of the present invention can be administered to a subject by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively or concurrently, administration can be by the oral route. The dosage administered will be dependent upon the age, health, and weight of the patient, kind of concurrent treatment, if any, frequency of treatment, and the nature of the effect desired.

The pharmaceutical compositions of the present invention can include pharmaceutically acceptable carriers comprising excipients and auxiliaries that facilitate processing of the active agents into preparations that can be used pharmaceutically. The pharmaceutical preparations of the present invention are manufactured in a manner that is, itself, known, for example, by means of conventional mixing, granulating, dragee-making, dissolving, or lyophilizing processes.

Formulations for parenteral administration include aqueous solutions of the active compounds in water-soluble form, for example, water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

It is well known that apoptosis, and particularly Bax mediated apoptosis, is centrally involved in the pathogenesis of many human illnesses and injury states. The following references describe the Bax protein playing a key role in various diseases: Injury-induced neuron death-Deckwerth, et al. Neuron. 17:401-411,1996; Martin, et al., J. Compo Neurol. 433:299-311, 2001; Kirkland, et al., J. Neurosci. 22:6480-90, 2002; Alzheimer disease-MacGibbon, et al., Brain Res. 750:223-234, 1997; Selznick, et al., J. Neuropathol. Exp. Neurol. 59:271-279, 2000; Cao, et al., J. Cereb. Blood Flow Metab. 21:321-333, 2001; Zhang, et al., J. Cell Biol. 156:519-529, 2002; Ischemia induced cell damage-Kaneda, et al., Brain Res. 815: 11-20, 1999; Gibson, et al., Mol. Med. 7:644-655, 2001; HIV (AIDS) and Bax: Castedo, et al., J. Exp. Med. 45 194:1097-1110, 2001; Drug-induced neuron death-Dargusch, et al., J. Neurochem. 76:295-301, 2001; Parkinson's disease-Ploix and Spier, Trends Neurosci. 24:255, 2001; Huntington's disease-Antonawich, et al., Brain Res. Bull. 57:647-649, 2002.

Therefore, in another embodiment, a pharmaceutical composition of the present invention can be administered to a subject for the treatment of an apoptotic disease. The method includes administering a therapeutically effective amount of a pharmaceutical composition comprising CPP to the subject. The term "therapeutically effective amount" refers to the amount of an inventive pharmaceutical composition required to reduce the severity and/or frequency of symptoms, elimination of symptoms and/or underlying cause, prevention of the occurrence of symptoms and/or their underlying cause, and improvement or remediation of disease. For example, a therapeutically effective amount of a pharmaceutical composition of the present invention encompasses the reduction of Bax mediated cell or tissue death in a subject.

Apoptotic diseases and related disorders as contemplated by the present invention, can include stroke, heart attack, ischemia, degenerative diseases (neuron and muscle, e.g., Alzheimer disease, Parkinson's disease, cardiomyocyte degeneration, etc), macular degeneration, hypoxia induced apoptosis, ischemia reperfusion injury, atrophy, infection by parasitic organisms (virus, bacteria, yeast, or protozoa, etc), side effects of other drugs (e.g., anti-cancer drugs), UV/X-ray irradiation, and several other pathological conditions triggering cell death signals.

As described above, the compositions described herein can be used to inhibit Bax mediated cell death wherein Bax overexpression in the cell is induced by chemo- and radio-therapy. In one exemplary embodiment, a pharmaceutical composition described above in accordance with the present invention can protect megakaryocytes from chemotherapy induced apoptosis without substantially affecting the ability of megakaryocytes to produce and release platelets.

It is further contemplated that the pharmaceutical compositions in accordance with the invention can be used in a combination therapy or adjunctive therapy with antiproliferative agents or chemotherapeutic agents for the treatment of proliferative disorders, such as neoplastic disorders or cancer. The phrase "combination therapy" embraces the administration of the pharmaceutical compositions including CPPs and a therapeutic agent as part of a specific treatment regimen intended to provide a beneficial effect from the co-action of these therapeutic agents.

Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The apoptotic disease treated by the combination therapy can include proliferative diseases, such as neoplastic disorders (e.g., leukemia) and cancer. Besides being useful for human treatment, the combination therapy is also useful for veterinary treatment of companion animals, exotic and farm animals, including rodents, horses, dogs, and cats.

In another embodiment of the invention, the therapeutic agents administered in combination therapy with the inventive CPP pharmaceutical compositions can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous anti-neoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

The CPPs in accordance with the present invention allow the combination therapeutic agents and therapies of the present invention to be administered at a higher dose, that is, at a dose higher than has been conventionally used in clinical situations because of the risk of thrombocytopenia.

The present invention also provides a method of preserving tissues and organs for transfusions or transplantation. According to the present invention, the cells, tissue, or organ can be stored in and/or contacted with a composition including an effective amount of CPP. The effective amount of CPP is an amount effective to mitigate Bax mediated apoptosis of the cells, tissue, or organ of interest. In some embodiments, a composition for storing cells or organs can include an effective amount of CPP and an organ preservation solution. In some embodiments, the composition can further comprise a Ku70-derived BIP peptide.

Typically, the tissue or organ has been separated from its usual nutrient sources, e.g., the blood circulation of a living animal or person. Organ preservation solutions depend on contacting, storing and/or perfusing the organ with a supportive preservation solution designed to provide pH buffering, osmotic balance and/or some minimal nutritional support, e.g., in the form of glucose and a limited set of other basic nutrients. This approach is typically combined with reduction in organ temperature to just above the freezing point of water. This is intended to reduce the metabolic rate of organ tissues, thus slowing the consumption of nutrients and the production of waste products. Thus, in some embodiments, the CPP containing compositions of the present invention can be employed at the hypothermic ranges commonly used in the art, which can range from below 20° C. to about 4° C. These art-known preservative solutions include, for example, isotonic saline solutions, that may contain, in various proportions, salts, sugars, osmotic agents, local anesthetic, buffers, and other such agents, as described, simply by way of example, by Berdyaev et al., U.S. Pat. No. 5,432,053; Belzer et al., described by U.S. Pat. Nos. 4,798,824, 4,879,283; and 4,873,230; Taylor, U.S. Pat. No. 5,405,742; Dohi et al., U.S. Pat. No. 5,565,317; Stern et al., U.S. Pat. Nos. 5,370,989 and 5,552,267.

The term, "organ" as used herein encompasses both solid organs, e.g., kidney, heart, liver, lung, pancreas, as well as functional parts of organs, e.g., segments of skin, sections of artery, transplantable lobes of a liver, kidney, lung, and other organs. The term, "tissue" refers herein to viable cellular materials in an aggregate form, e.g., small portions of an organ, as well as dispersed cells, e.g., cells dispersed, isolated and/or grown from heart muscle, liver or kidney, including bone marrow cells and progeny cells, blood born stem cells and progeny, and the various other art-known blood elements, unless otherwise specified.

The invention also contemplates using a CPP containing composition for localized or systemic circulatory or perfusion support for organs or tissues acutely deprived of normal blood circulation caused by trauma, e.g., infusions or temporary circulation of the inventive compositions to support a partially severed limb, or analogous conditions, until surgical repair of damaged vasculature is achieved.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

We show in the following example that interferon gamma receptor beta chain (IFNγR2) is a Bax inhibitor not belonging to the Bcl-2 family of proteins.

IFNγR2 is part of the interferon γ (IFN γ) receptor complex composed of IFNγR alpha chain (IFNγR1) and IFNγR2. IFNγR2 interacts with Jak2 prior to IFNγ binding. Upon IFNγ binding, a conformational change in the receptor complex occurs, followed by auto-phosphorylation of Jak kinase, phosphorylalion of IFNγR1, and recruitment of STAT1, leading to STAT1 activation. IFNγR2 is expressed in the plasma membrane, endoplasmic reticulum (ER) and mitochondria. At present, the biological significance of the mitochondrial localization of IFNγR2 is not known. IFNγR2 knock-out mice show no sensitivity to IFNγ and are unable to prevent infection by Lsteria monocytogenes. Previous studies showed that IFNγR2 plays a role in apoptosis regulation as a signal-transduction molecule of IFNγ (reviewed in ref. 19), but to our knowledge, there is no report describing the apoptosis regulating activity of IFNγR2 itself.

Here we report that the C-terminus of IFNγR2 has a Bax-inhibiting activity that is independent of the Jak/STAT signal transduction pathway. We also found that certain cancer cell lines (DAMI cells, MDA-MD468 cells and PC3) express a truncated form of IFNγR2 containing the C-terminal Bax-inhibitory domain. The presence of this C-terminal fragment of IFNγR2 in the cytosol may help such cancer cells increase their resistance to cytotoxic stresses, including those elicited by chemo- and radiotherapy.

Yeast-based Functional Screening for Bax Inhibitors

The yeast strain EGY48 was used for the yeast functional screening for Bax inhibitors. Mouse Bax was expressed under a galactose-inducible promoter using pGilda vector as reported. Yeast expression libraries of cDNAs of mouse brain and a human cell line (HeLa) were prepared in pYES2 and pJG4-5 vectors, respectively.

Cell Culture and Transfection Cell Culture

HT1080 (wild type, IFNγR2 null mutant and JAK2 null mutant) cells were cultured in Dulbecco's Modified Eagle's Medium (DMEM) supplemented with 10% fetal bovine serum (FBS). HeLa, Human Embryonic Kidney (HEK) 293 and HEK293T cells were purchased from ATCC, and cultured in DMEM supplemented with 10% FBS. LNCap and PC3 cells were purchased from ATCC and cultured in DMEM F12 medium supplemented with 10% FBS. RWPE1 and RWPE2 were purchased from ATCC and cultured in keratinocytes-SFM plus supplements medium (Gibco). Primary mammary epithelial (4A100) cultures were derived from organoids isolated from discarded mammary tissue acquired from patients undergoing reduction mammoplasty surgery. Anonymized specimens were acquired from patients who had given written consent, through the Tissue Procurement and Histology Core Facility of the Case Comprehensive Cancer Center (Case CCC), under a Case CCC IRB approved protocol. Primary epithelial cultures were grown in M87A+X medium. Human HME1 cells (Clontech) were grown in medium 171 with mammary epithelial growth supplement (Cascade Biologics) and penicillin-streptomycin.42 Human breast cancer cell line MDA-MD468 was cultured in RPMI, 5% FBS, supplemented with L-glutamine, penicillin-streptomycin and fungizone (Gibco). Human megakaryocytic cell line DAMI cells was cultured in Iscove's Modified Dulbecco's Medium (IMDM) supplemented with 10% horse serum. Human umbilical vein endothelial cells (HUVEC) were cultured in endothelial cell growth medium with supplements (EGM®-2-Endothelial Cell Medium-2-Lonza).

Transfection

Cells were cultured overnight in DMEM supplemented with 10% FBS. The transfections were performed using SUPERFECT® (Qiagen, Valencia, Calif.) in accordance with the manufacturer's instructions. Transfection efficiency was analyzed by the expression of the EGFP-tagged proteins.

Lentivirus

Five E. coli clones expressing pLKO1-shRNA IFNγR2 plasmids were purchased from Open Biosystems (cat #RHS4533-NM_005534). Lentiviruses were produced in HEK293T cells by transfection using each of pLKO1-shRNA IFNγR2, pCMV DR 8.76 and pMD2G. Viruses were produced and used to infect HeLa cells with a 1:3 dilution of stock lentivirus for 16 h. Cells were then cultured for 24 h in complete medium, and then stable clones expressing the shRNA against IFNγR2 and shRNA against GFP (control shRNA) were selected using puromycin. To select the best shRNA targeting IFNγR2 mRNA, cell lysates were analyzed by western blotting, and the best cloneshowing the lowest IFNγR2 protein expression was used to determine the effects of IFNγR2 knock-down in HeLa cells.

Apoptosis Detection

Apoptosis was induced by transfecting the cells with pcDNA3-human Bax, or pcDNA3-human Bak, or pcDNA3-human Bim EL, or by treatment with etoposide (10 μM) or staurosporine (100 nM). To determine the induction of apoptosis by different apoptotic stresses, cells were stained with Hoechst 33258 dye, and the numbers of cells with apoptotic nuclei were counted using fluorescence microscopy. Three hundred cells were analyzed in triplicate samples. The data presented in the figures showed the percentage of apoptosis ±SEM of three independent experiments. Caspase activity were measured by using a fluorogenic caspase 3 substrate II (Calbiochem), IFNγR2 constructs were cloned in pEGFP-C2 (IFNγR2wild type, IFNγR2$_{1-295}$ and IFNγR2$_{296-337}$) vector.

Apoptosis Induction by Overexpression of Bax, Bak or Bim

For Bax, Bak or Bim EL overexpression, cells were transfected with either 1 μg pcDNA3-human Bax, 1 μg pcDNA3-human Bak, or 1 μg pcDNA3 human Bim EL, and 4 μg of pEGFP plasmid encoding IFNγR2, and the apoptosis or caspase activity was determined 24 h after the transfection.

Immunoprecipitations

IFNγR2-Bax Co-immunoprecipitation (Co-IP)

HEK293T cells were lysed in 300 μl NP40 buffer (150 mM NaCl, 10 mM HEPES at pH 7.4 and 1% NP40) or CHAPS buffer (150 mM NaCl, 10 mM HEPES at pH 7.4 and 1% CHAPS) supplemented with protease inhibitors (1:100 dilution of protease inhibitor Cocktail; Sigma) and PMSF. Samples were pre-cleared by incubating 300-μl (1,000 mg total protein) cell lysates with 20 μl protein-G-sepharose (Amersham Biosciences) at 4° C. for 1 h. Then, the samples were incubated with 20 μl protein-G-sepharose pre-absorbed with 2 μg of Bax monoclonal antibody (B9, Santa Cruz) or IFNγR2 monoclonal antibody (Fitzgerald) at 4° C. for 2 h. After the incubation, sepharose beads were washed with lysis buffer. Beads were then boiled in 30 μl Laemmli buffer, and 15 μl of the sample was analyzed by western blotting. Western blotting analysis of pre-immunoprecipitation (Input) (100 μg total protein) and immunoprecipitated samples (IP) were performed with a Bax monoclonal antibody (B9 antibody, Santa Cruz), Bax polyclonal antibody (N20 antibody, Santa Cruz), or IFNγR2 polyclonal antibody (Fitzgerald).

Binding of Recombinant Proteins

Recombinant human Bax ΔTM (Bax C terminal transmembrane truncated human Bax) was produced by using pHMTc vector downstream of maltose binding protein (MBP), separated by the TEV protease site. Overexpressed MBP-Bax was purified through a maltose-binding column (NEB) and subsequently cleaved by TEV protease (Invitrogen), followed by Ni-affinity purification to remove the protease and the His-tagged MBP. IFNγR2 cytoplamic domain (amino acids 263 337) was fused with thioredoxin (rTrx) to increase the recovery rate from bacterial lysates. The production and the purification of this fusion protein were performed by Protein X Laboratory (San Diego, Calif.). Recombinant Bax (25 ng) was loaded onto Sepharose G beads pre-equilibrated with anti-Bax antibody (Bax B9, Santa Cruz) or pre-immune IgG (control IgG) at 4° C. for 2 h. The excess Bax molecules were washed 3 times with buffer (50 mM phosphate buffer, pH 7.4). Recombinant IFNγR2 (263-337)-rTrx (25 ng) was added to the beads preloaded with Bax and anti-Bax or control IgG. Beads and IFNγR2$_{263-337}$-rTrx were incubated at 4° C. for 2 h. After the incubation, beads were extensively washed with the loading buffer (50 mM phosphate buffer, pH 7.4). Beads were boiled in Laemmli buffer, and the supernatant was collected as a sample. Samples were analyzed by western blot using anti IFNγR2 antibody (C20, Santa Cruz) and Bax (N20, Santa Cruz).

Determination of the Effects of Bcl-2 and BIP on IFNγR2-Bax Interaction

HEK293T cells were lysed by using either NP40 buffer (150 mM NaCl, 10 mM HEPES at pH 7.4 and 1% NP40) or CHAPS buffer (150 mM NaCl, 10 mM HEPES at pH 7.4 and 1% CHAPS) supplemented with protease inhibitors (1:100 dilution of protease inhibitor Cocktail; Sigma) and PMSF, as previously reported.14 To determine if recombinant Bcl-2 (Prospect cat #PRO-630) protein competes with endogenous IFNγR2 for binding to endogenous Bax, HEK293T cell lysate prepared in NP40 buffer was used. Three-hundred microliters (1,000 μg total protein) of the sample was pre-cleared by incubating in 20 μl protein G-sepharose (Amersham Biosciences) at 4° C. for 1 hour.

Cleared samples (300 μl) were incubated (4° C. for 2 h) with or without recombinant Bcl-2 (75 or 150 nM final concentration) in the presence of protein G sepharose (20 μl) preabsorbed with 2 μg of Bax polyclonal antibody (BD Biosciences). Beads were washed and then boiled in 30 μl Laemmli buffer, and 15 μl of the eluted protein solution was analyzed by western blotting. Western blotting of pre-immunoprecipitation (pre-treated) (100 μg total protein) and immunoprecipitated samples (IP) were performed with IFNγR2 monoclonal antibody (Fitzgerald-WB), Bcl-2 monoclonal antibody (Santa Cruz), and Bax polyclonal antibody (HRP-conjugated N20 antibody, Santa Cruz). To determine the effects of BIP15 on the interaction of endogenous IFNγR2 and Bax, HEK293T cell lysate prepared in CHAPS buffer was used. Three hundred microliters of the sample was pre-cleared by incubating with 20 μl protein G-sepharose (Amersham Biosciences) at 4° C. for 1 h. Cleared samples (300 μl, 1,000 μg total protein) were incubated (37° C. for 2 h) with or without BIP (40 or 200 μM final concentration) in the presence of protein G sepharose (20 μl) preabsorbed with 2 μg of FNγR2 monoclonal antibody (Fitzgerald). Beads were washed and then boiled in 30 μl Laemmli buffer, and 15 μl of the eluted protein solution was analyzed by western blotting. Western blot analysis of Bax was performed by using Bax polyclonal antibody (N20, Santa Cruz).

Inhibition of Bax Activation by IFNγR2

HeLa cells were transiently transfected with pEGFP-C2-IFNγR2 (wild type 1-295, or 296-337) using SUPERFECT® (Qiagen, Valencia, Calif.) in accordance with the manufacturer's instructions. Four micograms of the plasmid were used to transfect cells cultured in 6-cm diameter dishes. After 24 h of transfection, the cells were treated with staurosporine (100 nM) for 3 h. Then, the cells were washed with phosphate buffer pH 7.4 (PBS), fixed using paraformaldehyde (1%), permeabilized with Triton X-100 (0.02%), blocked with goat serum, and the activation of Bax was analyzed by immunocytochemistry using monoclonal Bax 6A7 antibody (BDPharmingen) and ALEXA FLUOR® 568-labeled anti-mouse IgG secondary antibody (Invitrogen).

Determination of Concentrations of Endogenous IFNγR2 and Bax in Cultured Cells

Recombinant BaxΔTM and IFNγR2263-337-rTrx were used as standards. Cells were harvested and lysed in NP40 buffer (10 mM HEPES, 150 mM NaCl and 1% NP40 pH 7.4), or with hypotonic buffer for subcellular fractionation (20 mM HEPES, 10 mM KCl, 1.5 mM $MgCl_2$, 1 mM EDTA and 250 mM sucrose); both buffers were supplemented with protease inhibitors cocktail (Sigma) and PMSF (Sigma). LDH, F1α and YY1 proteins were used as makers of the cytosolic, mitochondrial and nuclear fractions, respectively. Cell lysates from equivalent cell numbers, and sequential dilutions of protein standards were subjected to SDS-PAGE (BioRad). Bax antibody conjugated with horseradish peroxidase (HRP) (anti-Bax N20-HRP, Santa Cruz) was used to detect Bax, and IFNγR2 antibody (C-20, Santa Cruz) was used to detect IFNγR2. HRP-conjugated anti-rabbit goat IgG was used as a secondary antibody. Signal intensities were analyzed by using BioRad Gel Doc and Quantity One 4.5.1 software from BioRad.

Protein Identification by Mass Spectrometry

To enrich for the immunoreactive (ir) IFNγR2 fragment expressed in transformed cells, DAMI and HEK293T cell lysates were incubated with anti-IFNγR2 antibody (C-20, Santa Cruz) overnight at 4° C., and the antibody-protein complexes were recovered by incubation of the mixture with protein G sepharose. The sepharose gels were then boiled in 30 μl Laemmli buffer, and 15 μl of the eluted protein solution was used for 1D-SDS-PAGE and western analysis. From a Coomassie blue-stained Tris-HCl gel, bands running between the protein markers for 10 and 15 kDa were collected. Proteins were reduced by DTT, alkylated by iodoacetamide and digested by trypsin overnight. The tryptic peptides were extracted from the gel by using 60% acetonitrile in 0.1% formic acid. Recombinant Trx-tagged IFNγR2$_{263-337}$ was used as positive control for the LC-MS/MS analysis. The tryptic peptides were analyzed by LC-MS/MS using a LTQ Orbitrap XL linear ion trap mass spectrometer (Thermo Fisher Scientific, Waltham, Mass.) coupled to an Ultimate 3000 HPLC system (Dionex) in the Case Center for Proteomics. The LC-MS/MS analysis was performed as follows: peptide solutions were injected into a reverse phase Aclaim PepMap 100 C18 column (3 mm, 100 Å, 150 mm×75 mm, Dionex Corporation, Sunnyvale, Calif.). Mobil phases used were: 2% acetonitrile, 0.1% formic acid in water (solvent A), and 80% acetonitrile, 0.1% formic acid (solvent B). A linear gradient of solvent B from 0% to 60% over a period of 60 min was used at a flow rate of 300 mL/min. Three specific peptide ions that are expected to be produced from IFNγR2 were selected with a mass window of 3 amu and subjected to MS/MS analysis with a normalized collision energy of 35%. These ions were: m/z 670.4 (z=2, DPTQPILEALDK (SEQ ID NO: 11)), 868.9 (z=2, DDVWDSVSIISFPEK (SEQ ID NO: 12)), and 754.4 (z=3, YWFHTPPSIPLQIEEYLK (SEQ ID NO: 13)). LTQ injection time was set to 2 s and automatic gate control target was 10,000 ions. The results from the LC-MS/MS analysis were subjected to an NCBI nr (version 20070216, containing 4626804 sequences) database search using Mascot Daemon Version 2.2.0 with a mass toleranceset to 2 Da for the precursor and 1 Da for the product ions. In addition to the targeted analysis, the remaining digest was also analyzed by data-dependent LC MS/MS.

The Cytoplasmic C-terminal Portion of IFNγR2 is a Bax Inhibitor

To perform a yeast-based functional screen for Bax inhibitors, yeast expression cDNA libraries were generated from purified mRNAs of human HeLa cells and mouse brain tissue using pJG4-5 and pYES2 vectors, respectively. As previously reported, two clones encoding the C-terminus of Ku70 were found as Bax suppressors in this screening (FIG. 1A). In the same experiment we also obtained a clone from the HeLa cell library encoding the cytoplasmic domain of IFNγR2 (IFNγR2$_{263-337}$; amino acids 263-337 of IFNγR2) (FIG. 1A and B) as a Bax suppressor. IFNγR2$_{263-337}$ contains a Jak2-binding domain (amino acids 284-295). To determine the role of the Jak2-binding domain in Bax inhibition, two IFNγR2 mutants were generated (FIG. 1B) and tested for their anti-Bax activity in human cells as described below. One mutant, IFNγR2$_{296-337}$, encodes amino acids 296-337 of IFNγR2 and does not contain the Jak2-binding domain; the other mutant, IFNγR2$_{1-295}$, encodes amino acids 1-295, retaining the Jak2-binding domain but not the C-terminal 41 amino acids of the receptor subunit.

IFNγR2 inhibits Bax-mediated apoptosis. IFNγR2$_{296-337}$ as well as IFNγR2wild type were able to inhibit apoptosis induced by Bax overexpression in HEK293 cells (FIG. 2A). On the other hand, IFNγR2$_{1-295}$ could not protect cells from Bax (FIG. 2A). These results suggest that the Bax-inhibiting domain localizes to the 41 amino acid sequence of the C-terminus of IFNγR2, and that Jak2-STAT1 signaling activated by IFNγ is not necessary for Bax inhibition. To confirm that IFNγR2 does not require Jak2-mediated signaling for Bax inhibition, human cell lines lacking IFNγR2 and Jak2 were examined. These cell lines were derived from the HT1080 human fibrosarcoma cell line. In these experiments, etoposide, a DNA topoisomerase II inhibitor, was used to induce apoptosis because etoposide is known to activate the Bax-mediated intrinsic cell death pathway. IFNγR2$_{296-337}$ and IFNγR2wild type were both able to inhibit etoposide-induced apoptosis in these cells, but IFNγR2$_{1-295}$ could not (FIG. 2B-E). These results support the hypothesis that IFNγR2 can rescue cells from apoptosis independent of Jak2-mediated signal transduction.

IFNγR2 Knock-Down Increases Apoptosis in HeLa Cells

To determine whether endogenously expressed IFNγR2 has a physiological role in suppressing apoptosis, IFNγR2 was knocked down by shRNA. HeLa cells were transfected with lentivirus that expresses shRNA targeting IFNγR2 mRNA. HeLa cells transfected with empty vector (pLKO1) or an shRNA targeting GFP mRNA were used as controls (FIG. 3A). IFNγR2 knock-down increased the sensitivity of HeLa cells to etoposide-induced apoptosis (FIG. 3B). Importantly, the basal level of apoptosis was also increased by IFNγR2 knock-down (FIG. 3A). These results suggest that IFNγR2 has a significant role in determining the cell-death sensitivity in HeLa cells.

IFNγR2 Inhibits Apoptosis Induced by Bim but not Bak

Bim is a BH3-only protein, which triggers Bax-mediated apoptosis. IFNγR2wild type as well as IFNγR2$_{296-337}$ were able to inhibit apoptosis induced by Bim overexpression (FIG. 4A). This result suggests that IFNγR2 is able to suppress Bim-dependent Bax activation. On the other hand, IFNγR2 could not rescue cells from apoptosis induced by Bak overexpression (FIG. 4B), suggesting that IFNγR2 specifically inhibits Bax-mediated apoptosis.

Subcellular Localization of IFNγR2-GFP

FIG. 5 shows HeLa (FIG. 5A-H) and HEK293 (FIG. 5I and J) cells expressing IFNγR2-GFP fusion proteins. IFNγR2wild type-GFP was detected in the plasma membrane, cytosol and a mitochondrion-like structure (FIG. 5C, D, I and J) as previously reported. In HeLa cells expressing IFNγR2wild type-GFP, GFP signal was detected mostly in the cytosol and plasma membrane (FIGS. 5C and D), though a weak punctate pattern of GFP signal suggestive of mitochondrial localization was also detected (the image of this pattern was very difficult to capture due to the strong GFP fluorescence in the cytosol and plasma membrane). In the case of HEK293 cells, IFNγR2wild type-GFP localized to a more definite mitochondrionlike structure that was captured in the image (FIG. 5I and J).

IFNγR2$_{296-337}$-GFP was detected in the cytosol of both HeLa (FIGS. 5E and F) and HEK293 cells (not shown). IFNγR2$_{1-295}$-GFP was detected in the cytosol, plasma membrane and the mitochondrialike structures in HeLa (FIGS. 5G and H) and HEK293 cells (not shown). In HeLa cells, GFP signal from the mitochondria-like structure was more evident in cells expressing IFNγR2$_{1-295}$-GFP than cells expressing IFNγR2wild type-GFP (FIG. 5C, D and K).

Western Blot Analysis of IFNγR2-GFP

IFNγR2-GFP expression in IFNγR2-null (mutant HT1080) cells was determined by western blot analysis using GFP antibody (FIG. 6A). Estimated molecular weights of IFNγR2wild type-GFP, IFNγR2$_{1-295}$-GFP and IFNγR2$_{296-337}$-GFP, are approximately 67 kDa, 64 kDa and 34 kDa, respectively. Proteins that have similar molecular weights were detected by GFP antibodies (FIG. 6A), suggesting that IFNγR2-GFP were expressed in these cells. Interestingly, we observed that IFNγR2$_{1-295}$-GFP migrated slower than IFNγR2wild type-GFP in every western blotting experiment performed in this study (FIGS. 5A and C). Since the estimated molecular weight of IFNγR2$_{1-295}$-GFP is smaller than IFNγR2wild type-GFP, this observation was unexpected. At present, we do not know the exact reason for this phenomenon, but a posttranslational modification such as glycosylation may be the cause of the slower migration of this mutant protein in SDS-PAGE.

Western blot analysis of IFNγR2-GFP expression was also performed using HEK293 cells (FIG. 6B-D). Although IFNγR2$_{296-337}$-GFP was detected at its estimated molecular weight (FIG. 6B), IFNγR2wild type-GFP and IFNγR2$_{1-295}$-GFP could not be detected in a simple western blot using GFP antibodies in HEK293 cell lysates. To verify the expression of IFNγR2-GFP fusion proteins (both wt and mutants), cell lysates were subjected to GFP immunoprecipitation and samples were further analyzed by IFNγR2 antibodies (FIGS. 6C and D). After enrichment of the GFP-tagged proteins, expression of IFNγR2wild type-GFP and IFNγR2$_{1-295}$-GFP was confirmed by monoclonal antibody recognizing the N-terminus of IFNγR2 (FIG. 6C), and IFNγR2$_{296-337}$-GFP expression was confirmed by antibodies detecting the C-terminus of IFNγR2-GFP (FIG. 6D).

There were GFP-antibody-positive bands with slightly higher and lower molecular weight than GFP (29 kDa) in cells transfected with pEGFP C2-IFNγR2wild type and pEGFP C2-IFNγR2$_{1-295}$ (bands marked with * in FIGS. 6A and B). We speculate that protease-dependent cleavage of IFNγR2-GFP fusion proteins produced these fragments. Protease inhibitors were present in the cell lysis buffer; therefore, it is likely that this cleavage occurred in the cells prior to preparation of the cell lysate, though further careful study will be needed to reveal the reasons for the appearance of these bands.

IFNγR2 Inhibits Bax Activation

Bax activation involves exposure of the protein's N-terminus by a conformational change followed by Bax translocation from the cytosol to mitochondria. Exposure of the N-terminus of Bax can be monitored by immunohistochemistry using 6A7 Bax monoclonal antibody (6A7 Ab) recognizing an epitope in the N-terminus of Bax. Staurosporine (STS), a pan-kinase inhibitor, 30 was used to induce the Bax conformational change. STS treatment (100 nM, 3 h) induced Bax activation that was detected by 6A7 Ab as shown in FIG. 7A. GFP expression itself did not inhibit Bax activation (FIG. 7A). IFNγR2$_{296-337}$-GFP as well as IFNγR2wild type-GFP (FIGS. 7C and D) inhibited STS-induced Bax activation. On the other hand, IFNγR2$_{1-295}$-GFP did not inhibit Bax activation (FIG. 7B). The percentages of 6A7 Ab-positive cells in GFP-positive cells were calculated and the results are shown in FIG. 7E. The inhibition of Bax activation by IFNγR2$_{296-337}$-GFP as well as IFNγR2 wild type-GFP was statistically significant (FIG. 7E).

IFNγR2 Directly Interacts with Bax

To examine whether IFNγR2 can bind Bax, we performed co-immunoprecipitation of endogenously expressed Bax and IFNγR2 in HEK293T cells (FIG. 8). It is known that certain detergents such as NP40 artificially activate Bax whereas CHAPS does not. Interestingly, Bax and IFNγR2 were co-immunoprecipitated by anti-Bax antibody in buffers containing either NP40 or CHAPS (FIG. 8A). This interaction was also observed when anti-IFNγR2 was used for immunoprecipitation and anti-Bax was used for Bax detection in western blot (FIG. 8B). Furthermore, the direct interaction of purified recombinant proteins of BaxΔTM (in which the c-terminal transmembrane (TM) domain is deleted) and IFNγR2263-337 (tagged with thioredoxin (rTrx)) was confirmed. These results suggest that the C-terminus of IFNγR2 directly binds Bax.

Bcl-2 Competed with IFNγR2 to Bind Bax In Vitro

Since it is known that Bcl-2 binds and inhibits Bax, we examined whether Bcl-2 has any influence on the IFNγR2-Bax interaction in vitro. Interestingly, addition of recombinant Bcl-2 protein (a truncated form without the C-terminal transmembrane domain to increase solubility in the buffer) to the HEK293T cell lysate interferes with the interaction of Bax and IFNγR2. In this experiment, NP40-based buffer was used because the Bcl-2-Bax interaction is known to be observed in this buffer. This result suggests that Bcl-2 and IFNγR2 recognize the same domain of Bax. We also examined the effects of Bax inhibiting peptide (BIP) designed from the Bax-binding domain of Ku70. Because Ku70 and BIP are known to bind the inactive form of Bax in CHAPS-based buffer, we used CHAPS-based buffer to examine the effects of BIP. As shown in FIG. 8E, BIP did not cause a significant inhibition of the Bax-IFNγR2 interaction. Three independent experiments were performed, and we observed results similar to that in FIG. 8E in two of the experiments. In one experiment, BIP caused a detectable reduction in the amount of IFNγR2 protein pulled down by Bax antibody (data not shown); however, this effect was not reproducible.

Expression of Cytoplasmic IFNγR2 in Transformed Cell Lines

IFNγR2C20 antibody (C20 Ab) recognizes the C-terminal 20 amino acids of IFNγR2 as an epitope. This antibody detected a small fragment (approximately 10 kDa) in western blot analysis of cell lysates prepared from megakaryocytic cancer cells (DAMI) and SV40-transformed kidney cells (HEK293T), but not from normal primary cultured cells (HUVECs) (FIG. 9A). This small fragment was enriched by immunoprecipitation (FIG. 9B), digested by trypsin and its identity was determined by targeted LC-MS/MS analysis. As a result, it was confirmed that a tryptic peptide derived from the C terminus of IFNγR2, DPTQPILEALDK (SEQ ID NO: 11), was present in the sample. Expression of this C-terminal fragment was also detected in two cancer cell lines, MDA-MD468 (breast cancer cell line) and PC3 (prostate cancer cell line) (FIG. 9C). Interestingly, the C-terminal fragment of IFNγR2 was not detected in normal mammary epithelial cells (4A100) or in non tumorigenic immortalized breast (HME-1) and prostate (RWPE-1) cells. These results suggest that a certain protease expressed in malignant tumorigenic cells may produce the antiapoptotic cytoplasmic fragment derived from IFNγR2.

Intracellular Concentrations of IFNγR2 and Bax

The approximate intracellular protein concentrations of IFNγR2 and Bax were determined by densitometric analysis of western blots using purified recombinant proteins as standards (FIGS. 10A and B). For IFNγR2, densitometric analysis was performed on a band corresponding to nonglycosilated full-length INFγR2 (approximately 37 kDa). For Bax, the density of a band corresponding to the full length of Bax (approximately 21 kDa) was measured. As there are other forms (glycosylated, truncated, etc.) of IFNγR2 and Bax, the estimated protein concentration in this experiment may underestimate the actual total expression levels of these proteins in cells.

However, our attempt to obtain an estimate of the stoichiometry of Bax and IFNγR2 will help determine our working hypothesis of how IFNγR2 regulates Bax-mediated apoptosis in the cell. First, the concentrations of Bax and IFNγR2 in total cell lysate (i.e., no fractionation) were measured. The ratio of Bax to IFNγR2 was approximately 1:1, 3:1 and 2:1 in HUVECs, DAMIcells and HEK293T cells, respectively. Next, the concentrations of Bax and IFNγR2 in the cytosol, nucleus and heavy membrane (mitochondria-rich fraction) were measured using DAMI cells and HEK293T cells. The Bax:IFNγR2 ratio in the cytosolic fraction was 2:1 and 3.5:1 in DAMI cells and HEK293T cells, respectively. The ratio in the heavy membrane fraction of DAMI cells and HEK293T cells was approximately 1.5:1 and 6:1, respectively. Interestingly, Bax and IFNγR2 were also detected in the nuclear fraction (FIG. 10). Because the nuclear fraction contains ER membranes attached to the cytosolic surface of the nucleus, the estimated concentration of Bax and IFNγR2 in the nuclear fraction is expected to be higher than the actual concentration in the nucleus.

EXAMPLE 2

In this Example, we examined the effect of oligomeric Aβ on the regulation of Bcl-2/Bim/Bax and its functional importance in neuronal cell death in the organotypic hippocampal culture and mouse model for Aβ toxicity.

Materials and Methods

Materials

Anti-β-actin antibody was obtained from Millipore (Billerica, Mass., USA) and anti-cleaved-caspase-3 antibody was obtained from Cell Signaling Technology (Danvers, Mass., USA). A β peptide (A $β_{1-42}$) and reverse control peptide (A $β_{42-1}$) were purchased from AnaSpec (Fremont, Calif., USA). PI and other chemicals were obtained from Sigma (St. Louis, Mo., USA).

Preparation of Oligomeric Aβ

Soluble oligomeric Aβ was prepared from synthetic peptide according to a previous paper. Briefly, 1 mg of $Aβ_{1-42}$ peptide was dissolved in 120 ml of hexafluoroisopropanol for 60 min at room temperature, and placed back on ice for 5-10 min. After evaporation of hexafluoroisopropanol overnight in the hood at room temperature, the peptide was dissolved in 40 μl of fresh anhydrous DMSO, and further diluted to 5 mM stock solution. The stock peptide solution was then incubated for 24 h at 4 1C., and centrifuged at 14 000×g for 10 min at 4° C. Supernatant was used as oligomeric Aβ. Before we treated slice culture with oligomeric Aβ, the oligomers were incubated at room temperature for 20 h.

Mouse Strains

Bax KO mice (strain name: B6.129×1-Bax $t^{m1\text{-}Sjk}$/J.) were purchased from The Jackson Laboratories (Bar Harbor, Me., USA). This Bax KO mouse has C57BL/6 genetic background. Bax KO mice were crossed with wild-type C57BL/6 mice, and bax$^{+/-}$ mouse colony was generated. Bax KO as well as WT mice used for this study were generated by crossing bax$^{+/-}$ 1 mice in our mouse colony. Each experiment used a set of Bax KO and WT mice obtained from the same parent to minimize variations caused by genetical differences among mice. Bax$^{-/-}$ mice were genotyped by PCR, as described previously. Conditions were set as follows: 941 C, 3 min (1 cycle); 941 C, 30 s, 631 C, 1 min, 721 C, 1 min (35 cycles); 721 C, 2 min (1 cycle).

Electron Microscopy

A $β_{1-42}$ was adsorbed onto carbon films supported on Formvar (EMS, Hatfield, Pa., USA) membrane-coated nickel grids. The excess buffered-protein solution was removed, and negatively stained with 2% uranyl acetate. Grids were then washed by touching the buffer and the excess buffer was immediately blotted using Whatman (Picataway, N.J., USA) filter paper. Grids were then air-dried and kept at room temperature. Negatively stained specimens were observed by a JEOL 1200EX electron microscope (JEOL, Tokyo, Japan) with 80 kV of electron acceleration voltage.

Preparation of Organotypic Hippocampal Slice Cultures

Organotypic hippocampal slice cultures were prepared as described previously. Briefly, hippocampal slice cultures were prepared using 7-10-day-old mouse pups. Slices were cut at 400 μm on a Mcllwain tissue chopper, transferred to Millicell membrane inserts (0.4 mm; Millipore), and placed in 6-well culture plates. The culture medium consisted of basal Eagle's medium with Earle's balanced salt solution, 20% heat-inactivated horse serum, enriched with 5.6 mM glucose. The medium was changed every other day. The effect of oligomeric Ab (500 nM) was tested in the slices that had been maintained for 11-14 days in vitro. Aβ oligomer or reversed sequence of $Aβ_{1-42}$ control peptide ($Aβ_{42-1}$) was added to cultures in serum-free medium and, after the treatment, the hippocampal slices were rinsed twice in ice-cold phosphate-buffered saline (PBS), and then harvested by removing the Millicell membrane insert.

Assessment of Neuronal Cell Death in Organotypic Hippocampal Slice Cultures

To determine neuronal cell death in the hippocampal slices, PI (5 µg/ml) was added to the slice culture medium. Images were acquired through an AxioCam camera on an Axiovert 200M microscope (Zeiss, Oberkochen, Germany). Fluorescent intensity was measured using Image J (NIH, Bethesda, Md., USA). Hematoxylin and eosin (H&E) and Nissl staining was also performed for routine histochemical and morphological analyses.

Protein Extraction and Western Blot Analysis

After oligomeric Aβ treatment, the slices were rinsed twice with ice-cold PBS and then lysed in ice-cold cell lysis buffer (Cell Signaling Technology) with protease and phosphatase inhibitor cocktail (Roche, Indianapolis, Ind., USA). The protein concentration was determined by BCA assay (Pierce, Rockford, Ill., USA). The extracted proteins were separated on 10 or 12% SDS-polyacrylamide gel and transferred onto polyvinylidene difluoride membranes. The blots were blocked with 10% non-fat milk in TBS-T for 1 h at room temperature, and then treated with primary antibodies diluted with 1% non-fat milk and incubated overnight at 4° C. The following antibodies were used for western blot analysis: anti-caspase-3 (1:1000; Santa Cruz Biotechnology, Santa Cruz, Calif., USA), anti-Bim (1:1000; Stressgen, Farmingdale, N.Y., USA), anti-Bcl-2 (1:1000; Stressgen) and 6A7 (conformational specific Bax antibody) (1:1000; BD Pharmingen, San Diego, Calif., USA).

Intrahippocampal Injection of Oligomeric Ab

C57BL6/J mice (The Jackson Laboratories; 2-3-month-old) were anesthetized with pentobarbital and placed in a stereotaxic frame. Injection was made using a 10-µl microsyringe (Hamilton, Reno, Nev., USA). A volume of 1 ml of oligomeric Aβ dissolved at 50 µM in PBS was injected into the left hippocampus. Control animals were prepared identically and injected with the same volume and concentration of $A\beta_{42-1}$ in PBS. Injections were made at stereotaxic coordinates from bregma; antereoposterior (AP)=2.3 mm, mediolateral (ML)=2.5 mm and doroventral (DV)=−2.5 mm according to a previous report. This corresponds to a site in the dorsal hippocampus in the apical dendritic zones of the CA1 region near the hippocampal fissure. Mice were killed 10 or 20 days after injection, brains dissected out, fixed in 10% buffered-formalin and paraffin-embedded. For brain tissue sections, 6-µm-thick serial sections were cut, mounted onto slides and rehydrated according to standard protocols.

Immunocytochemistry

Cultured hippocampal slices were rinsed with icecold PBS once and fixed for 2 h with 4% paraformaldehyde in 0.1M PBS. After washing with PBS, sections were permeabilized overnight with PBS containing 0.2% Triton X-100. At the end of the permeabilization blocking solution, 10% normal goat serum in PBS was applied for 4 h at room temperature. After washing with PBS, primary antibody was added and incubated for 24-48 h at 4° C. After thorough washing of the sections in PBS, a secondary antibody labeled with either Alexa Fluor (Life Technologies, Grand Island, N.Y., USA) 488 or 568 (1:300) was added and incubated for 4 h at room temperature. All of the experiments contained at least one sample incubated without a primary antibody to exclude non-specific signal. Nuclei were visualized with DAPI. Images were acquired through an AxioCam camera on an Axiovert 200M microscope (Zeiss). Images were then analyzed with the Axiovision software (Zeiss).

TUNEL Analysis

Detection of 3'-OH termini of DNA strand breaks was performed using in situ cell death detection kit (Roche). Briefly, the tissue sections were treated with proteinase K (20 µg/ml in 10 mmol/l Tris-HCl, pH 7.4) for 30 min at 37° C. after rehydration. After rinsing with PBS, TUNEL reaction mixture containing terminal deoxynucleotidyl transferase and fluorescence-labeled nucleotide was applied for 1 h 37° C. The samples were then washed and mounted using Aquamount (Southern Biotech, Birmingham, Ala., USA).

Results

Oligomeric Aβ Induces Bim Upregulation and Bcl-2 Downregulation in Hippocampal Slice Culture To characterize oligomeric Aβ in this study, we synthesized Aβ peptide, and then denatured the peptide and allowed oligomers to form, as described for Aβ-derived diffusible ligands. Consistent with previous findings for oligomeric Aβ our oligomeric Aβ preparations contain spherical particles visible by negative staining with transmission electron microscopy, and western blots show that the preparations contain various size of oligomeric proteins (FIG. 11).

Time-dependent changes of the levels of Bax, Bcl-2 and Bim were examined in oligomeric Aβ-treated brain slices. Oligomeric Aβ increased the expression of Bim but decreased the level of Bcl-2 (FIG. 12a). However, the level of Bax was not affected by oligomeric Aβ (FIG. 12a). As the N-terminus exposure is an early step of Bax activation that occurs in the cytosol, we analyzed this conformational change of Bax with a monoclonal antibody (6A7) recognizing the epitope in the N-terminus of Bax. Although the level of Bax expression was not affected by oligomeric Aβ, the number of 6A7-positive cells were significantly increased in oligomeric Aβ treated slice cultures (FIG. 12b), suggesting that oligomeric Ab induces Bax activation.

Ablation of Bax Reduces Oligomeric Aβ-induced Neuronal Cell Death in Hippocampal Slice Culture To further determine the functional role of Bax in oligomeric Aβ-induced neuronal cell death, hippocampal slice culture prepared from wild-type and bax$^{-/-}$ mice (FIGS. 13a and b) were used. Slices were treated with oligomeric Aβ in the presence of propidium iodide (PI), which penetrates cell membranes of dead or dying cells, and is widely used for evaluation of cell death. Although $A\beta_{42-1}$ peptide, a reverse sequence of $A\beta_{1-42}$, had no effect on PI uptake, the number of PI-positive cells was significantly increased in oligomeric Aβ-treated slices after 48 h of the treatment, indicating that oligomeric Aβ induces neuronal cell death in the hippocampal slice culture. However, the neuronal cell death induced by oligomeric Aβ was dramatically reduced in the slice culture from bax$^{-/-}$ mice (FIG. 13c). Nissl staining analysis further confirmed neuronal cell death by oligomeric Aβ in wild-type (WT) mouse slice culture but not in bax$^{-/-}$ mouse slice culture (FIG. 13d). These results indicate that Bax is a critical mediator for the neurotoxicity induced by oligomeric Aβ.

Intrahippocampal Injection of Oligomeric Aβ Increases Bim Expression and Active Forms of Bax To further examine the involvement of pro-apoptotic proteins in oligomeric Aβ-induced cell death, we determined the change of the levels of Bim and the active form of Bax in vivo. We injected oligomeric Aβ into the hippocampus and assessed its neurotoxicity. $A\beta_{42-1}$ was used as a control. Oligomeric Aβ injection into the WT mouse hippocampus induced neuronal cell death in 20 days after injection (FIG. 14a). The number of terminal dUTP nick-end labeling (TUNEL)-positive neurons was significantly increased by Aβ injection (FIG. 14b). To see the involvement of Bim and Bax, we measured the level of Bim and active form of Bax, and found that the level of Bim was dramatically increased as early as 10 days after oligomeric Aβ injection (FIG. 14c). The number of neurons containing the active form of Bax recognized by 6A7 antibody was also dramatically increased by Aβ injection (FIG. 14d). These data further support that both Bim and Bax have roles in oligomeric Aβ-induced neuronal cell death.

BIP Suppresses Neuronal Cell Death and Bax Activation Induced by Oligomeric Aβ in Hippocampal Slice Culture In this study, in addition to utilizing Bax knockout (KO) mice, we utilized BIP to examine the role of Bax in oligomeric Aβ-induced neurotoxicity. BIP used in this study consists of five amino acids, VPTLK, a sequence that is known to inhibit Bax activation. A mutated (scrambled) peptide, KLVPT, which does not bind Bax but has the same cell permeability, was used as a negative control. Both peptides were tagged with fluorescein isothiocyanate (FITC) so that intracellular delivery can be tracked by FITC signal. We first treated hippocampal slices with each peptide and analyzed green fluorescence to confirm their cell permeability, and confirmed that BIP and the control peptide equally penetrated neuronal cells after 24-h treatment (FIG. 15a). To determine whether BIP is able to suppress oligomeric Aβ-induced neuronal cell death in slice culture, either BIP or control peptide were co-applied with oligomeric Aβ. After 24-h treatment of oligomeric Aβ and the peptide, the treatment of BIP significantly prevented PI uptake, whereas the control peptide did not affect the level of PI uptake (FIG. 15b), suggesting BIP specifically blocks neuronal cell death induced by oligomeric Aβ. Consistent with the PI uptake results, both Niss1 staining and caspase-3 immunoblot analyses also showed that BIP significantly suppressed oligomeric Aβ-induced neuronal loss and caspase-3 activation, but control peptide failed to prevent neuronal cell death (FIGS. 15c and d). We also found that the treatment of BIP suppresses oligomeric Aβ-induced conformational change of Bax (FIG. 16). These results further support the hypothesis that the activation of Bax by oligomeric Aβ is an essential mechanism of oligomeric Aβ-induced neuronal cell death.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of inhibiting β-amyloid (Aβ) induced neuronal cell death, the method comprising:
administering to a neuronal cell exposed to a neurotoxic amount of Aβ a therapeutically effective amount of cell penetrating peptide (CPP), the CPP consisting of 5 to about 41 consecutive amino acids of SEQ ID NO: 1, the CPP comprising PILEA (SEQ ID NO: 2), and the CPP binding to Bax in the cell and inhibiting Bax mediated apoptosis in the cell.

2. The method of claim 1, the CPP consisting of SEQ ID NO: 1.

3. The method of claim 1, the CPP consisting of 5 to about 10 amino acids and including SEQ ID NO:2.

4. The method of claim 1, the CPP consisting of SEQ ID NO: 2.

5. The method of claim 1, wherein the neuronal cells are neuronal cells of a subject with Alzheimer's disease.

6. The method of claim 1 further comprising administering to the neuronal cell a Ku70-derived Bax-inhibiting peptide, the Ku70-derived Bax-inhibiting peptide having the following formula:

$$X^6PX^7LX^8X^9, \quad \text{(SEQ ID NO: 4)}$$

wherein $X^6$ is selected for amino acids with non-polar side chain;
$X^7$ is selected for amino acids with non-polar side chain;
$X^8$ is selected for amino acids with charged polar side chain;
$X^9$ is selected for amino acids with charged polar side chain; and
either $X^6$ or $X^9$ may be absent.

7. The method of claim 6, wherein the Ku70-derived Bax-inhibiting peptide is selected from the group consisting of VPMLKE (SEQ ID NO: 5), VPMLK (SEQ ID NO: 6), PMLKE (SEQ ID NO: 7), PMLK (SEQ ID NO: 8), VPTLK (SEQ ID NO: 9), and VPALR (SEQ ID NO: 10).

8. A method of inhibiting Bax induced neuronal cell death, the method comprising:
administering to the neuronal cell a therapeutically effective amount of cell penetrating peptide (CPP), the CPP consisting of 5 to about 41 consecutive amino acids of SEQ ID NO: 1, the CPP comprising PILEA (SEQ ID NO: 2), and the CPP binding to Bax in the cell and inhibiting Bax mediated apoptosis in the cell.

9. The method of claim 8, the CPP consisting of SEQ ID NO: 1.

10. The method of claim 8, the CPP consisting of 5 to about 10 amino acids and including SEQ ID NO:2.

11. The method of claim 8, the CPP consisting of SEQ ID NO: 2.

12. The method of claim 8, wherein the neuronal cell is exposed to a neurotoxic amount of Aβ.

13. The method of claim 8, wherein the neuronal cell is a neuronal cell of a subject with Alzheimer's disease.

14. The method of claim 8, further comprising administering to the neuronal cell a Ku70-derived Bax-inhibiting peptide, the Ku70-derived Bax-inhibiting peptide having the following formula:

$$X^6PX^7LX^8X^9, \quad \text{(SEQ ID NO: 4)}$$

wherein
- $X^6$ is selected for amino acids with non-polar side chain;
- $X^7$ is selected for amino acids with non-polar side chain;
- $X^8$ is selected for amino acids with charged polar side chain;
- $X^9$ is selected for amino acids with charged polar side chain; and
- either $X^6$ or $X^9$ may be absent.

15. The method of claim 14, wherein the Ku70-derived Bax-inhibiting peptide is selected from the group consisting of VPMLKE (SEQ ID NO: 5), VPMLK (SEQ ID NO: 6), PMLKE (SEQ ID NO: 7), PMLK (SEQ ID NO: 8), VPTLK (SEQ ID NO: 9), and VPALR (SEQ ID NO: 10).

* * * * *

SEQUENCE LISTING

```
<160> NUMBER OF SEQ ID NOS: 13

<210> SEQ ID NO 1
<211> LENGTH: 42
<212> TYPE: PRT
<213> ORGANISM: Homo sapiens

<400> SEQUENCE: 1

Lys Asp Pro Thr Gln Pro Ile Leu Glu Ala Leu Asp Lys Asp Ser Ser
1               5                   10                  15

Pro Lys Asp Asp Val Trp Asp Ser Val Ser Ile Ile Ser Phe Pro Glu
            20                  25                  30

Lys Glu Gln Glu Asp Val Leu Gln Thr Leu
        35                  40

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Pro Ile Leu Glu Ala
1               5

<210> SEQ ID NO 3
<211> LENGTH: 337
<212> TYPE: PRT
<213> ORGANISM: Homo sapiens

<400> SEQUENCE: 3

Met Arg Pro Thr Leu Leu Trp Ser Leu Leu Leu Leu Gly Val Phe
1               5                   10                  15

Ala Ala Ala Ala Ala Ala Pro Pro Asp Pro Leu Ser Gln Leu Pro Ala
            20                  25                  30

Pro Gln His Pro Lys Ile Arg Leu Tyr Asn Ala Glu Gln Val Leu Ser
```

```
                35                  40                  45
Trp Glu Pro Val Ala Leu Ser Asn Ser Thr Arg Pro Val Val Tyr Gln
 50                  55                  60
Val Gln Phe Lys Tyr Thr Asp Ser Lys Trp Phe Thr Ala Asp Ile Met
 65                  70                  75                  80
Ser Ile Gly Val Asn Cys Thr Gln Ile Thr Ala Thr Glu Cys Asp Phe
                 85                  90                  95
Thr Ala Ala Ser Pro Ser Ala Gly Phe Pro Met Asp Phe Asn Val Thr
                100                 105                 110
Leu Arg Leu Arg Ala Glu Leu Gly Ala Leu His Ser Ala Trp Val Thr
                115                 120                 125
Met Pro Trp Phe Gln His Tyr Arg Asn Val Thr Val Gly Pro Pro Glu
130                 135                 140
Asn Ile Glu Val Thr Pro Gly Glu Gly Ser Leu Ile Ile Arg Phe Ser
145                 150                 155                 160
Ser Pro Phe Asp Ile Ala Asp Thr Ser Thr Ala Phe Phe Cys Tyr Tyr
                165                 170                 175
Val His Tyr Trp Glu Lys Gly Gly Ile Gln Gln Val Lys Gly Pro Phe
                180                 185                 190
Arg Ser Asn Ser Ile Ser Leu Asp Asn Leu Lys Pro Ser Arg Val Tyr
                195                 200                 205
Cys Leu Gln Val Gln Ala Gln Leu Leu Trp Asn Lys Ser Asn Ile Phe
210                 215                 220
Arg Val Gly His Leu Ser Asn Ile Ser Cys Tyr Glu Thr Met Ala Asp
225                 230                 235                 240
Ala Ser Thr Glu Leu Gln Gln Val Ile Leu Ile Ser Val Gly Thr Phe
                245                 250                 255
Ser Leu Leu Ser Val Leu Ala Gly Ala Cys Phe Phe Leu Val Leu Lys
                260                 265                 270
Tyr Arg Gly Leu Ile Lys Tyr Trp Phe His Thr Pro Pro Ser Ile Pro
                275                 280                 285
Leu Gln Ile Glu Glu Tyr Leu Lys Asp Pro Thr Gln Pro Ile Leu Glu
                290                 295                 300
Ala Leu Asp Lys Asp Ser Ser Pro Lys Asp Asp Val Trp Asp Ser Val
305                 310                 315                 320
Ser Ile Ile Ser Phe Pro Glu Lys Glu Gln Glu Asp Val Leu Gln Thr
                325                 330                 335
Leu

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: X is an amino acid with non-polar side chain
<220> FEATURE:
<221> NAME/KEY: X
<222> LOCATION: (3)..(3)
<223> OTHER INFORMATION: X is an amino acid with non-polar side chain
<220> FEATURE:
<221> NAME/KEY: X
<222> LOCATION: (5)..(6)
<223> OTHER INFORMATION: X is an amino acid with charged polar side
      chain
```

```
<400> SEQUENCE: 4

Xaa Pro Xaa Leu Xaa Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Val Pro Met Leu Lys Glu
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Val Pro Met Leu Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Pro Met Leu Lys Glu
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Pro Met Leu Lys
1

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Val Pro Thr Leu Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10
```

```
Val Pro Ala Leu Arg
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Asp Pro Thr Gln Pro Ile Leu Glu Ala Leu Asp Lys
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Asp Asp Val Trp Asp Ser Val Ser Ile Ile Ser Phe Pro Glu Lys
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide

<400> SEQUENCE: 13

Tyr Trp Phe His Thr Pro Pro Ser Ile Pro Leu Gln Ile Glu Glu Tyr
1               5                   10                  15

Leu Lys
```